United States Patent
Bleiweiss et al.

(10) Patent No.: US 6,514,076 B1
(45) Date of Patent: Feb. 4, 2003

(54) PRECIPITATION HARDENABLE STAINLESS STEEL ENDODONTIC INSTRUMENTS AND METHODS FOR MANUFACTURING AND USING THE INSTRUMENTS

(75) Inventors: Richard Kim Bleiweiss, Bountiful, UT (US); Arno Schöler, Busswil (CH)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/848,078

(22) Filed: May 3, 2001

(51) Int. Cl.[7] .................................................. A61C 5/02
(52) U.S. Cl. ....................................................... 433/102
(58) Field of Search ................................ 433/102, 165, 433/224, 225; 451/48, 28

(56) References Cited

U.S. PATENT DOCUMENTS

| 5,041,118 | A | * | 8/1991 | Wasilewski | 606/85 |
|---|---|---|---|---|---|
| 5,125,838 | A | | 6/1992 | Seigneurin | 433/102 |
| 5,213,499 | A | | 5/1993 | Levy | 433/102 |
| 5,380,200 | A | | 1/1995 | Heath et al. | 433/102 |
| 5,464,362 | A | | 11/1995 | Heath et al. | 451/48 |
| 5,512,237 | A | * | 4/1996 | Stigenberg | 420/49 |
| 5,665,091 | A | * | 9/1997 | Noble et al. | 606/85 |
| 5,682,665 | A | * | 11/1997 | Svanberg | 29/458 |
| 5,855,844 | A | * | 1/1999 | Martin | 420/40 |
| 5,984,679 | A | | 11/1999 | Farzin-Nia et al. | 433/102 |

* cited by examiner

*Primary Examiner*—Todd E. Manahan
(74) *Attorney, Agent, or Firm*—Workman, Nydegger & Seeley

(57) ABSTRACT

Precipitation hardenable stainless steel endodontic files and methods for their manufacture, wherein the most preferred precipitation hardenable stainless steel is 17-4PH and aging is preferably not one of the manufacturing steps. Precipitation hardenable stainless steels used in embodiments of this invention are iron-chromium-nickel grades that have the desired properties of flexibility, strength, hardness, wear resistance, stiffness, resistance to permanent deformation, resistance to variable torque, and biocompatibility for endodontic files.

35 Claims, 7 Drawing Sheets

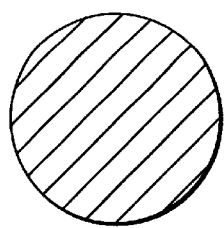
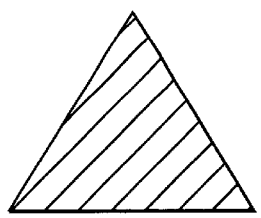
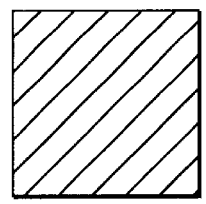
FIG. 4A　　　　　　FIG. 4B　　　　　　FIG. 4C
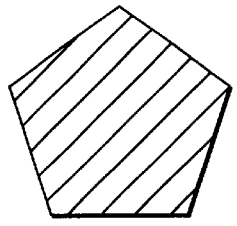
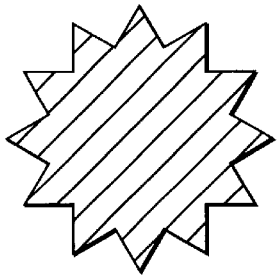
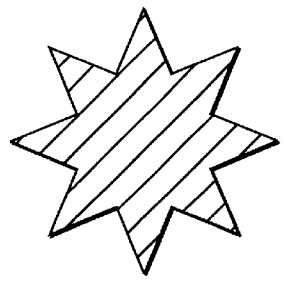
FIG. 4D　　　　　　FIG. 4E　　　　　　FIG. 4F
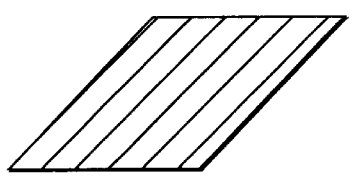
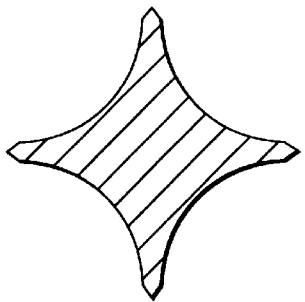
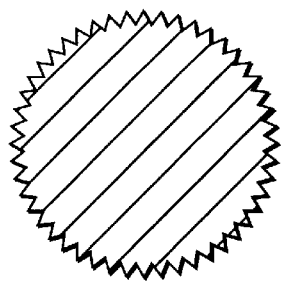
FIG. 4G　　　　　　FIG. 4H　　　　　　FIG. 4I
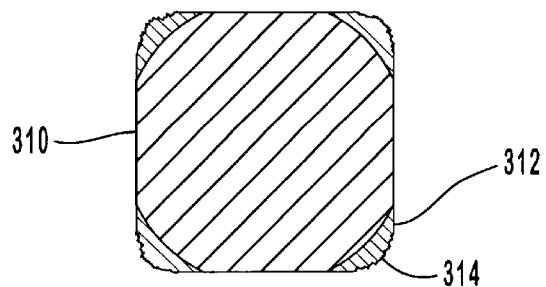
FIG. 4J

PRECIPITATION HARDENABLE STAINLESS STEEL ENDODONTIC INSTRUMENTS AND METHODS FOR MANUFACTURING AND USING THE INSTRUMENTS

BACKGROUND OF THE INVENTION

1. The Field of the Invention

The present invention relates generally to endodontic file instruments and methods for their manufacture. More specifically, the present invention relates to precipitation hardenable stainless steel endodontic instruments and methods for their manufacture that preferably do not include heat treatment.

2. Relevant Technology

To preserve a tooth with a pulp that is diseased or is potentially diseased, it is generally necessary to remove as much of the pulp material as is possible from the pulp canal of the tooth, to shape the root canal(s) without excessively weakening the root canal walls, to prevent or minimize the presence of bacteria through the use of irrigants and dressings, and lastly, to clean the walls of the root canal(s) by removing the smear layer created during instrumentation of the root canal(s). These steps are all done to prepare the root cavity for sealing or obturation which involves filling the root canal with biocompatible materials, such as gutta percha, before the pulp cavity is sealed, thereby promoting the healing and functional recovery of the tooth. This procedure is referred to as root canal therapy.

As indicated hereinabove, root canal preparation involves pulp removal, cleaning of the root canal walls and shaping of the canal walls. This is typically achieved through a guided procedure with the use of instruments which are moved either manually, mechanically or by combinations thereof These instruments are files or bits that are configured to bore and/or cut. Mechanical instrumentation can be achieved through the use of endodontic handpieces coupled to instruments such as files. The endodontic handpieces can impart rotational motion to a file, reciprocal motion by alternately rotating a file clockwise and counterclockwise, sonic movements or ultrasonic movements.

With regard to operating procedures, there are two basic methods from which all of the canal-preparation techniques can be derived. These methods have been interpreted by various authors in an operational context and also in terms of the instrumentation. The primary conventional systems and methods for removing pulp material from the root canal of a tooth are the apico-coronal (step-back) technique and the corono-apical (crown-down) technique. Although these conventional cleaning techniques both rely generally on sequential increases in the diameter of instruments inserted into the root canal. The step-back technique involves the sequential use of instruments by first inserting an instrument all the way down to the apex of the root canal and then using progressively larger and shorter files to clean the root canal. So the step-back technique involves cleaning the root canal from the apex toward the crown. The crown-down technique uses a set of files that are increasingly longer and smaller in diameter. So the crown-down technique involves first using a short and large diameter file to clean the upper portion of the root canal at the crown and then using a file that is longer and smaller until a file is used that reaches and cleans the apex. Each technique has its own unique benefits and disadvantages which are discussed hereinbelow.

As indicated above, in the step-back technique, the apical portion of the tooth is prepared first and then the remainder of the canal is flared from apex to crown. This process essentially involves inserting a series of progressively larger files into the apex of the root canal and rotating each file and/or moving the file up and down in a longitudinal motion until a file can be inserted that is considered to be a suitable standard size for completing the process or that meets some resistance to rotation. The rest of the canal is then flared by sequentially using each file in the set with each file being larger than the preceding file and by alternately advancing and then withdrawing each instrument.

With each increase in file diameter, the rigidity increases and the flexibility of the files decreases. As a result, it becomes increasingly difficult for the files to adjust to or to follow the contours of the perimeter surfaces of the root canal. This reduced flexibility also increases the likelihood that the files will fail to contact some portions while removing too much of the surrounding dentin in some areas through excessive abrasion and resulting in overthinning of the walls.

Not only is the completeness effected by the use of a set of files wherein each file is more rigid than the preceding file but the ability to safely move the file within the canal is also limited. More particularly, the increasing rigidity results in decreased ability to negotiate the curves in the canal. Significant problems that can result from inserting increasingly rigid files and also from initially inserting a file all the way down to the apex includes laceration and transportation of the apical foramen, as well as misdirection and perforation of the wall.

Another problem is the formation of ledges. Ledges can occur when a practitioner attempts to insert a file as far as the apex and the file is too inflexible to properly curve with the root canal or move around a protrusion. When a file is too inflexible to curve or flex as needed and is halted prematurely, the downward pressure exerted on the file, in conjunction with the tendency of the file to straighten itself, causes the tip of the file to dig into the side of the root canal and form a ledge. Such ledges are difficult to bypass; and if the ledge occurs very close to the apex, the ledge may give the practitioner the mistaken impression that the apex has been reached.

The crown-down technique generally involves the use of a set of file instruments wherein each file in the set of file instruments has a progressively different diameter at the top of the cutting portion of the file, i.e., the point where the file becomes smooth and no longer has cutting capabilities. The smooth portion may have a constant diameter. The diameter at the top of the cutting portion of each file may be either constant or graduated for the entire set of instruments such that the top of the cutting portion of each file is progressively smaller than that of the preceding file. By using such files, a very large area is initially abraded and a large borehole is formed in the root canal.

One example of the operational deficiency of the crown-down method lies in its association with instruments made of nickel/titanium (Ni/Ti). Based on the greater flexibility of files formed from nickel/titanium compared with files formed from steel, proponents of the crown-down method in conjunction with nickel/titanium files assert that such files can better follow the curvatures of a root canal. Additionally, it has been asserted that such files are more likely to stay in the center of the root canal, thereby decreasing the likelihood of ledging or perforating the root canal walls. As set forth hereinbelow in greater detail, each material has its own unique advantages and disadvantages.

Moreover, because nickel/titanium files are more flexible than steel files, they tend to follow the path of least resistance and therefore cannot be used, in the same way as steel files, to be applied actively and intentionally by the operator. As a result, even when the operator knows the thickness of a particular portion, such as an interference or obstruction which the operator desires to rectify or straighten, the operator lacks the freedom to aggressively drive the file as needed and clean the portions that are difficult to reach. Accordingly, when a nickel/titanium file is used to clean a non-cylindrically shaped root canal, the file moves only at the center of the canal and/or the area of least resistance and fails to remove all of the necrotic tissue.

Problems, such as overthinning of root canal walls, perforation of a root canal wall, excessively weakening of the walls of the tooth and a failure to fully contact all of the canal walls, can be easily caused by the passive, self-guiding use of nickel/titanium files with progressively larger tapers in the transition from the first instrument to the next one in the set, and increasing rigidity in accordance with the crown-down technique which prevents the files from being laterally moved to enable the files to clean the entire perimeter of the root canal.

It should also be remembered that while rotation of a set of passively actuated files, in the center of the canal, in accordance with the crown-down technique, may result in successful root canal therapy, there is a significant hazard due to the passivity of the instruments when linked to canal diameters and wall thicknesses that are still statistically unknown.

The flexibility of the files used in the crown-down technique, which are typically formed from nickel/titanium, prevents the files from being successfully urged against the perimeter or against the various surface features of the root canal. As also discussed above, the flexibility of the files also increases the tendency of the files to remain in the center or at the location where less resistance to movement is encountered. Accordingly, the flexibility of the files also contributes to a borehole configuration which substantially deviates from the original anatomy of the root canal.

There are also other disadvantages to the use of nickel/titanium files. The flexibility of nickel/titanium files increases the likelihood that the file may bend and be deformed upon encountering a hard substance. Since nickel/titanium files are more fragile and more flexible than stainless steel files, the nickel/titanium files can break more easily and unexpectedly than steel files. When a nickel/titanium file instrument is used with a large file diameter the flexibility decreases to the point of being as rigid as stainless steel and yet breaks more easily. More particularly, beyond a certain diameter, the upper halves of larger diameter files are still as rigid as that of steel files while the flexible lower halves of nickel/titanium file instruments are more prone to break.

Additionally, rotation of a file in a canal that has a laminar upper two-thirds exposes the tip of the file to the risk of breaking when the tip of the file is embedded or stuck in a canal whose diameter is smaller than its own diameter! To avoid breaking the tip when it is embedded or stuck in a canal whose diameter is smaller than the diameter of the tip, operators who use nickel/titanium files are advised to employ catheterization in order to obtain a prophylactic widening of the canal, using a series of instruments with increasingly larger tip diameters.

Another disadvantage of nickel/titanium files is that nickel embodied in the alloy may potentially result in an allergic reaction. Further, nickel/titanium files cost about four times as much as steel files and yet nickel/titanium files generally wear out faster than steel files. Nickel/titanium files wear out so quickly that some manufacturers mark their products as being intended for single use only.

Although stainless steel of various types has been used in the manufacture of endodontic files, this material has been generically disqualified as being unsuited for its use as a single material in the manufacture of endodontic files. Reasons for this disqualification of stainless steel include its lack of flexibility and its stiffness that can lead to undesirable edging.

A conventional form of stainless steel in the manufacture of endodontic files is known as 304 stainless steel in the USA and as 18-8 stainless steel in Europe. This form of stainless steel, which is similar to USA 316 stainless steel, has generally the shortcomings that have been described above regarding stainless steel endodontic file instruments. To avoid the shortcomings that are conventionally associated with stainless steel endodontic files, the trend in endodontic has been to use other materials such as Ni/Ti alloys, superelastic Ni/Ti alloys, and two-material substances. See, for example, U.S. Pat. Nos. 5,213,499, 5,380,200, and 5,984,679, which are hereby incorporated herein by reference in their entirety.

As revealed by the present state of the art, stainless steel endodontic files have sufficient hardness, but they are not flexible enough for effective endodontic work. Ni/Ti endodontic files are more flexible than stainless steel files, but their flexibility is excessive for certain applications, they are brittle, and have low tensile strength, which easily leads to file rupture upon application of a torque. Consequently, Ni/Ti endodontic files are regarded as inadequate for use with variable torque handpieces such as air-driven turbines, even though such turbines have many desirable features for driving dental instruments.

Because some materials have the desired hardness and other materials have the desired flexibility, endodontic files have been manufactured with more than one material. However, multi-material file manufacture tends to be more complex than single material file manufacture.

Based on the foregoing observations, methods and devices are needed in the endodontic arts which enable a dental practitioner to effectively use file instruments which are more resistant to wear, harder and less flexible than Ni/Ti instruments, but not as hard and resilient as stainless steel instruments.

It would also be an advancement in the endodontic arts to provide methods and devices which rely on materials that are flexible enough and that have enough tensile strength without being unduly brittle, and without exhibiting the allergenic effects of Ni/Ti materials.

It would also be a beneficial development in the endodontic arts to provide methods and devices which can be used with variable torque handpieces, such as air-driven turbines, in addition to their use in hand-held instruments.

Additionally, it would be an advancement in the endodontic arts to provide methods and devices that can rely on only one manufacturing material.

Finally, it would also constitute progress in the endodontic arts to provide methods and devices in which the file material is sufficiently hard and such hardness is achieved without requiring heat treatment.

OBJECTS AND BRIEF SUMMARY OF THE INVENTION

The present invention has been developed in response to the present state of the art and, in particular, in response to problems and needs that have not been solved heretofore.

An object of the present invention is to provide methods and devices that enable a dental practitioner to effectively use file instruments which are more resistant to wear, and which are harder and less flexible than Ni/Ti instruments, but not as hard and resilient as stainless steel instruments. An advantage of these features is that the devices according to the present invention are flexible while being stiff and hard enough to hold a sharp edge.

Another object of the present invention is to provide methods and devices that rely on materials which are flexible enough and which have enough tensile strength without being unduly brittle and without exhibiting the allergenic effects of Ni/Ti materials. An advantage of these features is that the devices according to the present invention are not so stiff as to easily cause ledging and are capable of withstanding stress without becoming plastically deformed or breaking.

An additional object of the present invention is to provide methods and devices that can be used with variable torque handpieces, such as air-driven turbines, in addition to their use in hand-held instruments. An advantage of this capability is that the devices according to the present invention are versatile and they can be effectively used in conjunction with an ubiquitous driver such as an air-driven turbine.

Additionally, another object of the present invention is to provide methods and devices that can rely on only one manufacturing material. An advantage of this manufacturing is that it reduces the complexity of the manufacturing process and it provides devices with the uniform properties of single material devices.

Finally, it is an object of the present invention to provide methods and devices in which the file material is sufficiently hard, and such hardness is achieved without requiring heat treatment. An advantage of this manufacturing feature is that it simplifies the manufacturing process because it requires fewer steps than conventional manufacturing processes that rely on heat treatment to impart the desired degree of hardness.

To achieve the foregoing objects, and in accordance with the invention as embodied and broadly described herein, file instruments according to the present invention comprise a file manufactured with a base material that is a precipitation hardenable stainless steel, preferably in the form of a type such as martensitic, semiaustenitic, and austenitic. The precipitation hardenable stainless steel according to the present invention is more preferably in the martensitic form, and most preferably a 17-4PH stainless steel.

Methods for manufacturing file instruments according to the present invention comprise the steps of providing a precipitation hardenable stainless steel base material and forming the material into a file. Files can be formed from the base material such as a precursor blank by an conventional method. Examples of conventional methods for forming a precursor blank or rod of base material into a file instrument include cutting lands into the rod, twisting the rod, abrading the rod, and combinations thereof Forming the file instrument may involve multiple steps such as imparting a desired longitudinal taper before cutting, twisting or abrading the precursor rod or blank used to form the file instrument. It may also be necessary to shape the precursor blank to provide a desired cross-sectional shape such as a triangular or square cross-sectional shape. The file instrument so obtained is preferably not subjected to heat treatment because it possesses the desired flexibility and tensile strength. When indentations or other features that are typically obtained by cutting are desired, such features can be cut into embodiments of the file instruments manufactured according to the present invention. The order in which cutting and twisting takes place is not a limiting feature of the methods of the present invention. This order is chosen in practice according to conventional machining preferences.

These and other objects, features, and advantages of the present invention will become more fully apparent from the following description, drawings, and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Same numbers used in different drawings label like features. Understanding that these drawings depict only typical embodiments of the invention and are not therefore to be considered to be limiting of its scope, the invention will be described and explained with additional specificity and detail through the use of the accompanying drawings in which:

FIGS. 4A–4J are transverse cross-sectional views of endodontic files.

DETAILED DESCRIPTION OF THE PREFERRED EMBODIMENTS

Figure 1:
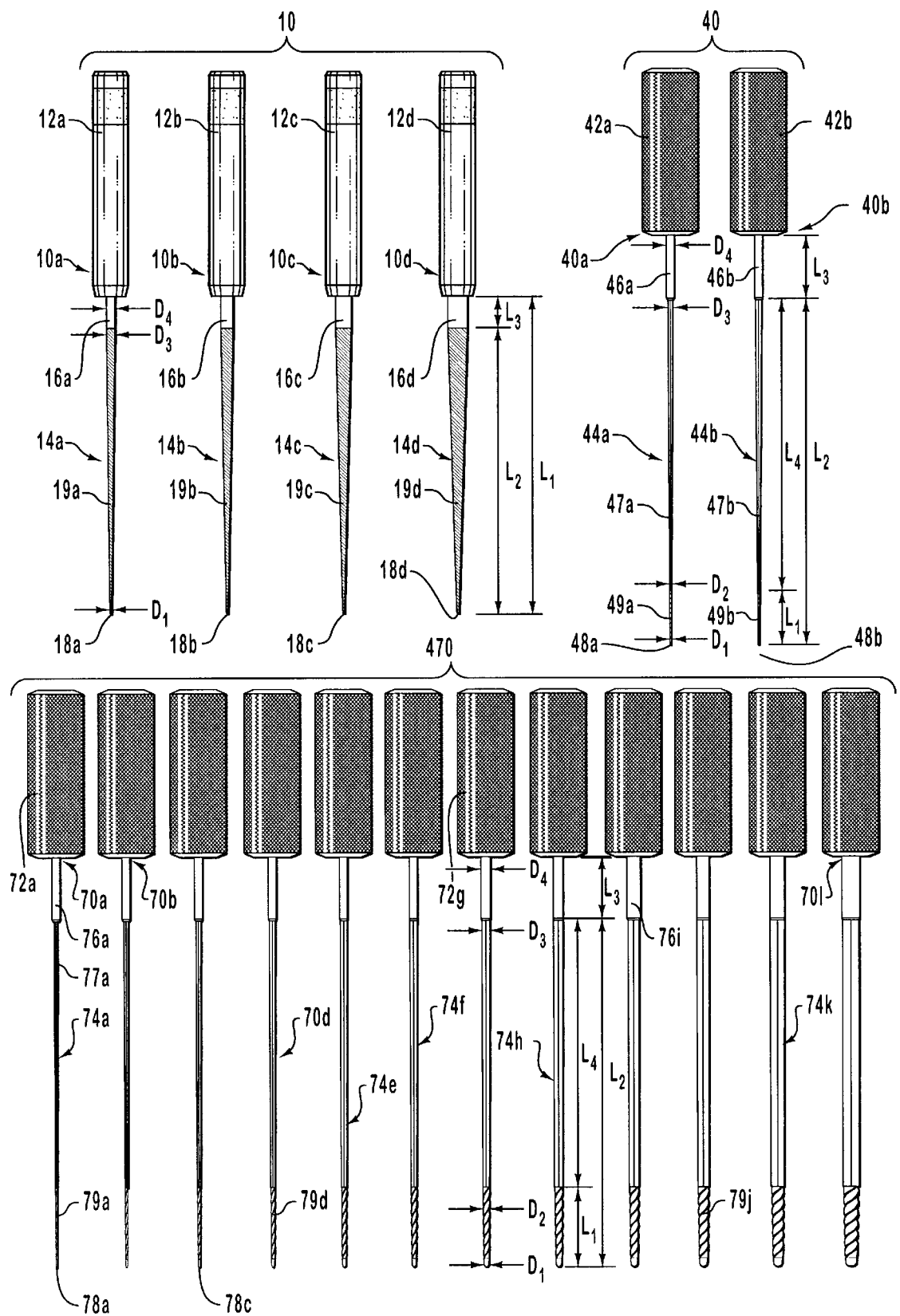
FIG. 1 is a view of a system of endodontic tools including a first set of instruments for cleaning the operative middle portion of an operative root canal, a second set of instruments for improving the access into the apical root portion and a third set of instruments for cleaning the apical root portion.

The present invention is directed to endodontic file instruments which are flexible but not as flexible and prone to rupture as Ni/Ti files, and which are not as stiff as conventional stainless steel files. Furthermore, the endodontic file instruments according to the present invention are hard enough to effectively hold a sharp edge without wearing as fast as Ni/Ti files. Since the files are more flexible than conventional stainless steel files, they are less likely to cause ledging.

As indicated above, stainless steel has been widely used in manufacturing endodontic files. Stainless steel is an alloy of Fe and chromium from less than 10% to more than 25%. The trend in endodontic files has been away from the use of stainless steel as Ni/Ti files have become increasingly popular due to their greater flexibility. Despite the conventional teachings regarding stainless steel and its disfavored use according to conventional endodontic file instrument manufacturing, it has been discovered in the context of the present invention that a type of stainless steel has unique mechanical properties that make it particularly useful for manufacturing endodontic files. This stainless steel is precipitation hardenable stainless steel. Endodontic files manufactured with precipitation hardenable stainless steel have superior properties relative to those of files that are manufactured with other materials such as Ni/Ti alloys, two-material substances and conventional stainless steel alloys. These superior properties relate to the desired flexibility, strength, hardness, wear resistance, stiffness, resistance to permanent deformation, resistance to variable torque, and biocompatibility for the manufacture of endodontic file instruments.

Precipitation hardenable (PH) stainless steels are iron-chromium-nickel alloys. Hardness for these alloys can be increased by precipitation hardening through an aging treatment of a martensitic or austenitic matrix with one or more of the following elements: Cu, Al, Ti, and Mo. Precipitation hardenable stainless steels are classified as austenitic, semiaustenitic, or martensitic depending on the solution-annealed microstructure, the martensite start and finish temperatures, and the behavior upon cooling from a suitable solution-treatment temperature. Aging by heating is part of the conventional treatment of these alloys for increasing their hardness. The aging treatment is sometimes supplemented with cold work.

While the alloys of the present invention may be any precipitation hardenable stainless steel, such as a PH stainless steels of types that are martensitic, semiaustenitic, and austenitic, a more preferred alloy is martensitic PH stainless steel. The most preferred alloys are alloys which are referred to with the designation 17-4PH.

For alloys including precipitation hardenable stainless steel, a wide range of properties can be obtained by varying the heat-treatment practice. The standard aging times conventionally used for aging temperatures of 480° C. and 510° C. (900° F. and 950° F.) are such that most steels so heat treated are in the fully aged or slightly overaged condition. See, for example, ASM Specialty Handbook, Stainless Steels, J.R. Davis (ed.), ASM International, The Materials Information Society, p. 35 (1994).

It has been discovered in the context of this invention that PH stainless steels which are not subjected to aging as in conventional practice are the most preferable form of PH stainless steel alloys for the manufacture of endodontic file instruments. This suitability derives from the characteristics of PH stainless steels that are not subjected to the conventional aging by thermal treatment. Such characteristics include a desired degree of flexibility, strength, hardness, wear resistance, stiffness, resistance to permanent deformation, resistance to variable torque, and biocompatibility.

Examples of embodiments of PH stainless steel endodontic file instruments according to the present invention are provided herein by providing examples of embodiments of such PH stainless steel alloys, and by providing examples of embodiments of such file instruments together with examples of their dimensions and shapes. Examples of embodiments of methods for the manufacture of PH stainless steel endodontic file instruments are provided herein by providing examples of processes for the manufacture of such files using PH stainless steel alloys.

In addition to "precipitation hardenable", other conventional terms that are used in connection with the stainless steel alloys of the present invention are "precipitation hardening" and "precipitation hardened". For conventional terms and techniques concerning stainless steels, see ASM Specialty Handbook, Stainless Steels, J.R. Davis (ed.), ASM International The Materials Information Society, pp. 6–10, 34–36, 59–61, 321 (1994), which is hereby incorporated herein by reference. The terms "precipitation hardenable" are preferred in the context of this invention because it has been discovered that the most preferred form of the stainless steel used in manufacturing embodiments of the present invention possesses the desired mechanical properties without requiring what in the art is known by terms such as heat hardening, aging and thermal aging. It is within the scope of the present invention to utilize stainless steel alloys that are hardened by heat as is conventionally done. However, it has been discovered that when endodontic file instruments are manufactured from PH stainless without heat hardening the instruments, then the instruments have mechanical properties that are more desirable. More particularly, non-heat hardened instruments have the optimal desired balance of flexibility and rigidity.

As indicated above, precipitation hardenable (PH) stainless steels are iron-chromium-nickel alloys. Embodiments according to the present invention are manufactured with iron-chromium-nickel stainless steels which optionally comprise additional minority constituents. These stainless steels comprise from about 10% to about 20% Cr, and from about 2% to about 35% Ni. Preferred compositions of such alloys comprise from about 12% to about 18% Cr, and from about 2% to about 20% Ni. More preferred compositions of such alloys comprise from about 12% to about 18% Cr, and from about 3% to about 10% Ni. Most preferred compositions of such alloys comprise from about 14% to about 18% Cr, and from about 2.5% to about 6% Ni.

As is customary in providing composition al information, percentages given herein are understood to refer to weight percentages unless it is otherwise indicated. Compositions given herein are provided according to conventional practice for stainless steel alloys. See, for example, ASM Specialty Handbook, Stainless Steel, cited above. According to this conventional practice, for example, the compositions do not refer explicitly to the amount of iron in the alloy.

PH stainless steel used in the manufacture of embodiments of endodontic files according to the present invention optionally comprise other constituents, such as at least one of the following constituents: Mn in amounts up to about 2.2%, Si in amounts up to about 1.2%, Mo in amounts up to about 3.5%, P in amounts up to about 0.05%, S in amounts up to about 0.05%, Cu in amounts up to about 5%, Al in amounts up to about 1.6%, Nb in amounts up to about 1%, Ti in amounts up to about 2.5%, V in amounts up to about 0.5%, C in amounts up to about 0.2%, N in amounts up to about 0.15%, and B in amounts up to about 0.01%.

As indicated above, the most preferred PH stainless steels used in the manufacture of embodiments of files according to the present invention are the martensitic alloys known by the designation 17-4PH. An embodiment of such 17-4PH stainless steels has the following composition: up to about 0.07% C, up to about 1.00% Mn, up to about 1.00% Si, from about 15.0% to about 17.5% Cr, from about 3.0% to about 5.0% Ni, up to about 0.04% P, up to about 0.03% S, from about 3.0% to about 5.0% Cu, and from about 0.15% to about 0.45% Nb. Another embodiment of such 17-4PH stainless steels has the following composition: up to about 0.07% C, up to about 1.00% Mn, up to about 1.00% Si, from about 15.0% to about 17.5% Cr, from about 3.0% to about 5.0% Ni, up to about 0.04% P, up to about 0.03% S, and from about 0.15% to about 0.45% Nb. Still another embodiment of such 17-4PH stainless steels has the following composition: up to about 0.07% C, up to about 1.00% Mn, up to about 1.00% Si, from about 15.0% to about 17.5% Cr, from about 3.0% to about 5.0% Ni, up to about 0.04% P, up to about 0.03% S, and up to about 0.15% Nb.

In terms of standard designation in the technology of stainless steel, preferred PH stainless steel used in the manufacture of embodiments of endodontic files according to the present invention include PH stainless steels such as PH15-7 Mo, 17-7PH, AM-350, AM-355, A-286, and JBK-75(b). More preferred PH stainless steels used in the manufacture of embodiments of endodontic files according to the present invention include PH stainless steels such as PH13-8 Mo, 15-5PH, Custom 450, and Custom 455. Embodiments of such stainless steels are provided hereinbelow in the form of Examples 1-58.

The PH stainless steel endodontic file instruments according to the present invention may be utilized in accordance with any methodology. For example, files formed from PH stainless steel may be utilized in accordance with the crown down methodology or the step back methodology. However, the PH stainless steel is preferably used to manufacture endodontic file instruments designed for use in accordance with a methodology disclosed in numerous patents and patent applications filed on behalf of Francesco Riitano and owned by Ultradent Products, Inc. of South Jordan, Utah. As explained in detail below, this methodology known as EndoEze® AET™ (Anatomic Endodontic Technology) owned by Ultradent Products, Inc. enables the instruments to be used in anatomical conformance with the shape of the root canal. U.S. patents that relate to this methodology include U.S. Pat. No. 6,045,362 entitled Endodontic Methods for Progressively, Sectionally and Anatomically Preparing Root Canals with Specific Instruments for each Section having Predetermined Working Lengths which was filed on Jan. 28, 1998; and U.S. Pat. No. 6,059,572 entitled Endodontic Methods for the Anatomical, Sectional and Progressive Corono-Apical Preparation of Root Canals with Three Sets of Dedicated Instruments which was filed on Jun. 3, 1999. U.S. applications related to this technology include U.S. patent application Ser. No. 09/492,566 entitled Endodontic Systems and Methods for the Anatomical, Sectional and Progressive Corono-Apical Preparation of Root Canals with Minimal Apical Intrusion which was filed on Jan. 27, 2000; U.S. patent application Ser. No. 3 09/536,821 entitled Endodontic Systems and Methods for the Anatomical, Sectional and Progressive Corono-Apical Preparation of Root Canals With Instruments Utilizing Stops which was filed on Mar. 27, 2000; and U.S. patent application Ser. No. 09/753,981 entitled Endodontic System and Methods for the Anatomical, Sectional and Progressive Corono-Apical Preparation of Root Canals with Dedicated Stainless Steel Instruments and Dedicated Nickel/Titanium Instruments which was filed on Jan. 3, 2001. For purposes of disclosure of the present invention, each of the foregoing patents and applications is incorporated herein by specific reference.

The EndoEze® EndoEze® AET™ (Anatomic Endodontic Technology) of Ultradent Products, Inc. referenced above involves the use of distinct instruments as are shown in FIG. 1 to clean and shape the anatomical root canal in different phases such that the root canal is cleaned progressively and sectionally. The instrument(s) associated with each phase have been designed specifically for that particular phase and accordingly have unique customized characteristics and features. The system of instruments shown in FIG. 1 are described hereinbelow in more detail after explaining the procedures for completing each phase with the different instruments shown in FIG. 1.

Figure 2A:
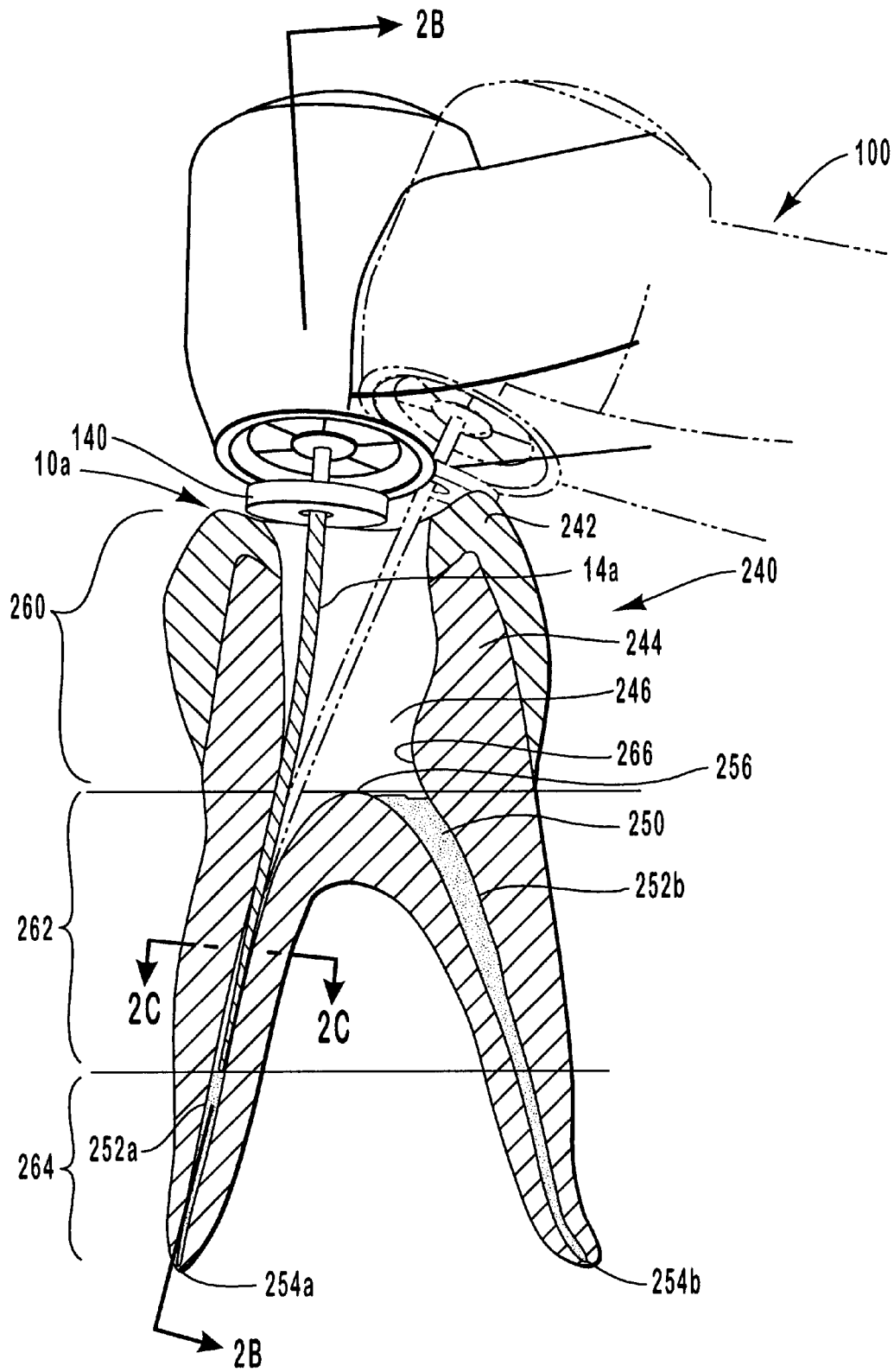
FIGS. 2A–2B show embodiments of PH stainless steel endodontic files operated by a driver, such as an electric motor or an air turbine.

The system of instruments shown in FIG. 1 includes three distinct sets. To appreciate the namenclature used for these sets, reference is made to FIGS. 2A–2B and 3 which depict a molar 240 in various stages of the root canal cleaning procedure. FIG. 2A depicts a root canal 252a being cleaned after the overhanging portions of enamel 242 and dentin 244 have been removed to provide access into pulp chamber 246 and after the pulp material 250 has been removed from pulp chamber 246. The sections of the operative root canal being cleaned in FIGS. 2A–2B include the operative coronal portion 260 and the operative middle portion 262. The apical portion 264 is shown being cleaned in FIG. 3.

The operative coronal portion 260 essentially includes the access cavity walls down to the floor 256 of pulp chamber 246. The operative middle portion 262 is the upper portion of the anatomical root canal while the apical portion 263 is the lower portion of the anatomical root canal. A typical apical portion 264 is the last or bottom 3 mm of the anatomical root canal. For example, the apical portion 264 of root canal 252a extends 3 mm above apex 254a.

Figure 2B:
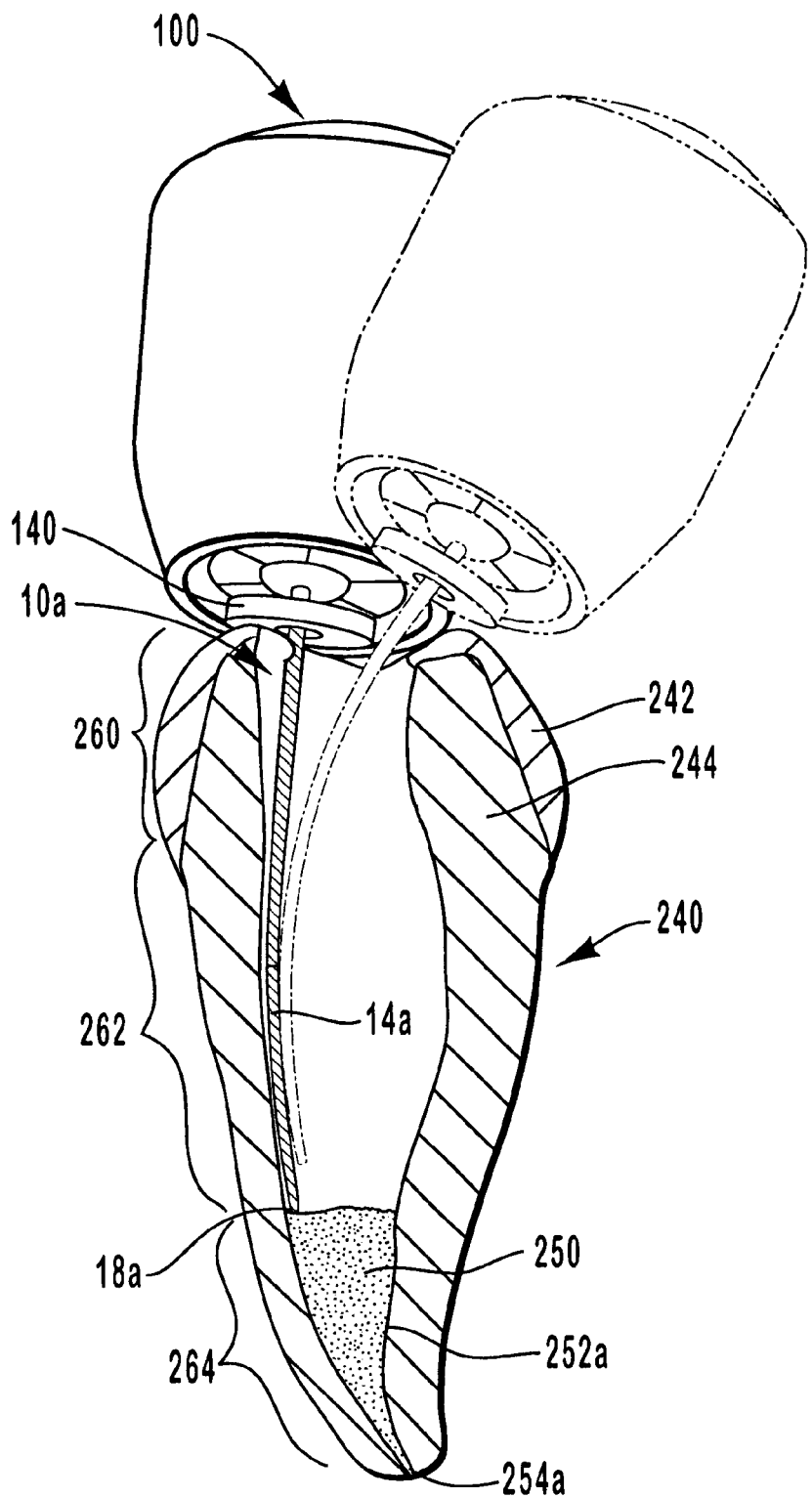
Figure 3:
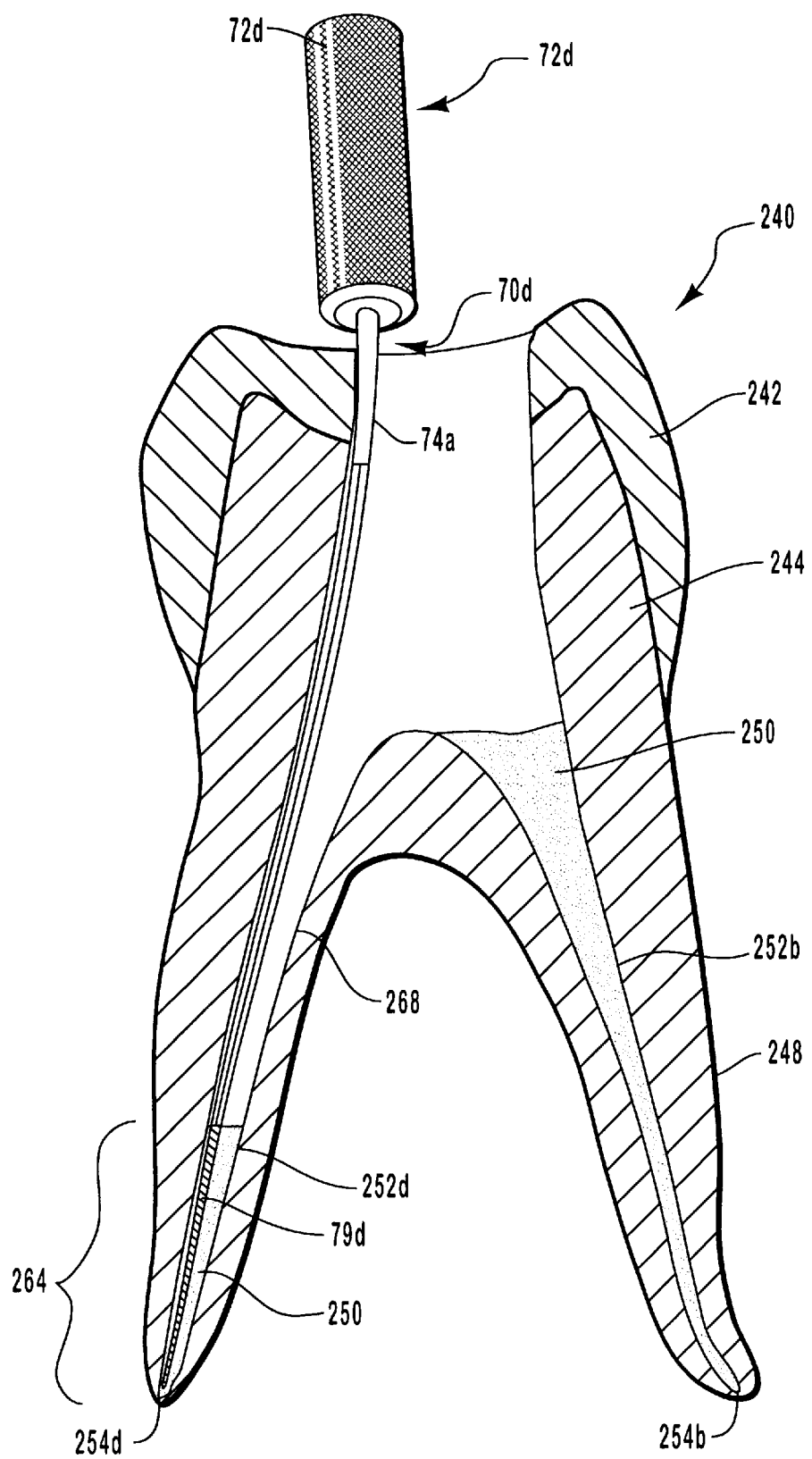
FIG. 3 is a longitudinal cross-sectional view of a tooth with a file inserted into a root canal having a length that is sufficient to reach the apex.

The three distinct set of instruments are namely a set of instruments for cleaning the operative middle portion identified as operative middle portion set 10; an optional set of instruments used to improve access into the apical root portion identified as optional set 40; and a set of instruments for removing and cleaning essentially all pulp material from the apical root portion that is identified as apical portion set 70. FIGS. 2A–2B depict file 14a of instrument 10a from operative middle portion set 10 being used to clean to clean the pulp material from the root canal operative middle portion 262 of tooth 240. Once operative middle portion 262 has been cleaned, then the apical portion 264 is cleaned as shown in FIG. 3 with one of the instruments from apical portion set 70 such as 70d. In some instances, it is necessary to use an instruments from optional set 40 before cleaning the apical portion in order to widen the transition from the operative middle portion 262 to apical portion 264.

The features of each set are provided below in detail in example 59. It should be understood, however, that each instrument has a file with a top end extending from a handle. File instruments can also be manufactured that are just a file without a handle. File instrument 10a has a file 14a extending from handle 12a. File 14a has a shank portion 16a and tines or an abrading portion 19a. The abrading portion extends from tip 18a to shank portion 16a. The features of the other files are similarly numbered.

Before utilizing an instrument from set 10a, the practitioner first identifies the combined length of the operative middle portion 262 and the operative coronal portion 260. The practitioner then selects a file instrument or a set of file instruments such as set 10 with a file length corresponding to the combined length of the operative middle portion length and the operative coronal portion. After removing the overhanging enamel 242 and dentin 244 with any suitable instrument, file 14a of file instrument 10a is then inserted into root canal 252, as shown in FIG. 2A, down through operative middle portion 262 without extending substantially into apical portion 264. Each file 14 of each file instrument in the set of instruments 10 shown in FIG. 1 has a length that is only sufficient to enable the file to contact the operative middle portion and the operative coronal portion of the root canal. Accordingly, a file instrument such as file instrument 10a or a set of file instruments such as 10 comprises a first endodontic instrument means for anatomically removing and anatomically cleaning essentially all pulp material from the operative middle portion without significantly removing pulp material from the apical root portion.

The file length of files 14a–b enables a practitioner to aggressively clean the operative middle portion without worrying that the instrument will overly thin the root canal, perforate the apex or that cleaning will cause extrusion of material through the apex. Another benefit of cleaning the operative middle portion 262 first is that the apical portion 264 is then generally more accessible and easily cleaned. Additionally, since instruments are selected for use in cleaning the operative middle portion 262 which have files lengths that do not permit entry into the apical portion 264, the likelihood of jamming or breaking a tip of an instrument while working in the confined space of the apical portion 262 is prevented.

By instrumenting in the operative middle portion 262 and the operative coronal portion 260 before the cleaning the apical portion, the practitioner can use an instrument according to the present invention that is relatively flexible compared to the conventional instruments. As shown in FIG. 2B, which is a cross-sectional view taken along cutting line 2B—2B of tooth 240 in FIG. 2A, file 14a of file instrument 10a is sufficiently flexible to be flexed against any surface of operative middle portion 262 or operative coronal portion 260 and yet is sufficiently rigid to remain flexed against the surface during a cleaning motion such as a longitudinal motion, a rotational motion or a reciprocating rotational motion. The file is also sufficiently resilient that substantial deformation of the file does not occur due to the forces experienced during cleaning of the pulp material from the root canal.

File instrument 10a is shown in FIGS. 2A–2B being moved in a longitudinal movement or up and down movement as well as being rotated while file 14a is flexed or arched to urge the file against the root canal surfaces. As shown, the configuration and mechanical properties of the files used to clean the operative middle portion 262, and preferably the operative coronal portion as well 260, enable a practitioner to move the files around the perimeter or from side to side to contact the perimeter. Such movements enable the file to follow the contours of the root canal. Further, since the file is moved around the perimeter, the file has more than one center of motion during cleaning of the operative middle portion of the root canal, such as a pivot point or center of rotation, as the tip of the file or at least a part of the abrading portion does not generally remain primarily in one position. While stainless steel is very useful for achieving the versatility in the effective types of motions used in accordance with cleaning the operative middle portion 262, greater flexibility is achieved when utilizing an instrument with a PH stainless steel file.

Due mainly to the configuration and mechanical properties of the files, the contours of the operative coronal portion and the operative middle portion can be used during their cleaning by a practitioner as a guide for the movements of the files as the files are pushed against the surfaces of the root canal and simultaneously moved around the perimeter or periphery of the root canal until the practitioner has reached the beginning location of the cleaning and shaping process. By adapting to the perimetrical or perimetral anatomy of the root canal, the entire perimeter or substantially all of the perimeter is contacted and cleaned along the length of the perimeter without substantially altering the configuration of the perimetrical anatomy. For example, in root canals that are primarily noncircular, the files can be urged along one side and then along the next side wall in a manner such that the resulting cleaned and shaped root canal is generally widened but still primarily noncircular. In other words, there is essentially no borehole that obviously corresponds to the shape of the file. Also since a perimetrical anatomy that was primarily tubular or laminar will be enlarged but will still be primarily tubular or laminar, the tooth is less likely to be weakened as compared with prior art methodologies.

Due to the ability to move the file as discussed, the anatomy of the root canal remains substantially unaltered despite the cleaning of essentially all pulp material from the operative middle portion. The understanding that the final anatomy is guided by the shape of the original anatomy enables a practitioner to more confidently urge a file such as file 14a against all surfaces of root canal 252 and aggressively clean all of the surfaces of operative middle portion of the root canal since the likelihood of overly thinning the root canal or causing lateral perforations is diminished.

Another advantage of the configuration and mechanical properties of operative middle portion instruments, such as file 14a shown in FIGS. 2A–2B, is that the file can simultaneously abrade both operative coronal portion 260 and operative middle portion 262. The files can simultaneously abrade both portions as each file has an abrading portion along the entire length of the file. A primary benefit of simultaneously abrading both portions is the ability to further straighten the operative coronal portion 260 while cleaning the operative middle portion 262.

Use of files in the operative middle portion which have an abrading portion along their entire length or along substantially all of their length such as abrading portions 19a–b is in contrast to files formed in accordance with ISO standardization. ISO standardized files have abrading portions of up to 16 mm and the remainder of the file is a smooth shank. Since such files are inserted down to the apex, it is generally not possible to abrade any portion beyond the anatomical root canal. Since such files frequently fail to remove interferences extending from the access or root chamber above the anatomical root canal, the instrument that is manufactured with conventional materials must bend around the interferences, thereby further increasing the likelihood of wall perforations, overthinning and failing to clean significant portions of the canal. It especially increases the likelihood of iatrogenic modifications resulting from the tip of the file. Manufacture of ISO standardized endodontic files according to the present invention should diminish the detrimental incidence of their deficiencies in endodontic practice.

File instrument 10a is preferably used in conjunction with an endodontic handpiece designed for movement of endodontic file instruments as shown in FIG. 2A at 100. The endodontic handpiece 100 and file 10a are drawn in phantom lines to represent the ability of the PH stainless steel file to be moved and flexed as root canal 252a is cleaned. File instrument 10a can be continuously rotated in one direction only or file instrument 10a can be rotated in a reciprocating motion such that file instrument 10a rotates for example, clockwise for half of a revolution and then counterclockwise for half a revolution. A reciprocating motion is preferred as such motion enables the file to alternately engage material 250 and the walls of the operative middle portion of the root canal in a manner that removes material 250 and to then rotate in the opposite direction such that the file less aggressively engages material 250 and the operative middle portion walls, depending on the file design. Accordingly, rotating file instrument 10a in a reciprocating motion minimizes breakage of file 14a when file 14a encounters a surface that prevents rotation of file instrument 10a in a direction that enables cleaning and removal of material 250. Breakage is further minimized by the use of embodiments of PH stainless steel file instruments due to the mechanical properties of the PH stainless steel alloys, particularly when not subjected to hardening. File instrument 10a can also be vibrated or manipulated by hand. Hand milling is, however, more difficult and time consuming. The optional stop 140 shown being utilized is generally not necessary since the file length can be selected to correspond closely with the combined length of the operative coronal portion and the operative middle portion.

As indicated above, it may be necessary in some circumstances to improve the access into the apical root portion before cleaning the apical root portion of the root canal. More particularly, it may be beneficial or necessary to widen the tract of the root canal to provide access for thin irrigation needles. This may be achieved by widening the transition between the operative middle portion 262 and the apical portion 264 or by widening the entire apical portion such that a thin irrigation needle can access the apical portion as needed. Thin irrigation needles typically have a diameter no smaller than about 0.30 mm so it may be necessary to increase the diameter of portions of the root canal up to about 0.35 mm or even up to about 0.40 mm, particularly within the region of the boundary between the operative middle portion and the apical root portion. Note that the diameter need only be slightly larger than a thin irrigation needle in order to provide adequate access. Improving access into the apical portion not only enables such irrigation needles to move as needed, it also reduces the likelihood that the thin irrigation needles will be blocked. Although FIG. 3 depicts file 74d inserted into apical portion 264 of root canal 252a cleaning the apical portion, use of instruments 40a or 40b of optional set 40 is achieved in essentially the same fashion. When utilized to widen the access into the apical root portion of a root canal, file 40a is first introduced followed sequentially by file 40b. A file instrument such as file instrument 40a or a set of file instruments such as 40a and 40c comprises a second endodontic instrument means for improving access into the apical root portion after the pulp material has been essentially removed from the operative middle portion by the first endodontic instrument means.

Figure 8:
FIG. 8 is a partial perspective view of an endodontic file depicting the tip of the file.
Figure 9:
FIG. 9 is a partial perspective view of an endodontic file depicting the tip of the file.

Each file instrument 70a–l comprises a handle 72a–l connected to a file 74a–l. Each file 74 has a top end where the file joins handle 72. When utilized to clean the apical root portion of a root canal, one file such as 70b or 70c is first introduced into the apical root portion followed by then next larger file such as 70c or 70d. Each file terminates at a tip 78a–l located opposite the top end of the file. Tips 78a–l can have any configuration, however, tips 78a–l preferably have minimal cutting capability to decrease the likelihood of ledging such as the tips shown in FIGS. 8–9. A file instrument such as file instrument 70a or a set of file instruments such as 70a–l comprises a third endodontic instrument means for removing and cleaning essentially all remaining pulp material from the apical root portion after the pulp material has been essentially removed from the operative middle portion.

When cleaning the apical portion 264 as shown in FIG. 3, the apical root portion file instruments are generally moved in a different pattern compared to the operative middle portion file instruments due primarily to the different perimeter anatomies of the two portions. A root canal generally becomes more cylindrical towards the apical portion such that a root canal with a perimeter anatomy that is essentially elliptical in shape within the operative middle portion tapers to an essentially cylindrically shaped perimeter anatomy within the apical portion.

An elliptical perimeter anatomy typically requires that the practitioner move the file around the perimeter and/or flex the rotating file against the surfaces or walls in a milling motion such that the tip is moved to many locations around the perimeter. Due to the more cylindrical anatomy of an apical root portion, it becomes much less necessary, and virtually impossible to flex a rotating file in a milling motion. It is generally adequate to merely rotate the file within the apical root portion and/or move the file in a longitudinal motion. More specifically, after the file reaches the apex or approximately reaches the apex, the file is preferably moved upward while simultaneously being rotated, and it is withdrawn in order to be cleaned before being reintroduced. Since the instruments used to clean the apical portion and to improve the access into the apical portion are typically moved by hand, they have a handle adapted for such use as shown at 42a–b and 72a–72l while the instruments used to clean the operative middle portion have handles 12a–b adapted for use with an endodontic handpiece.

Since an apical portion file is generally not moved around the perimeter as in cleaning the operative middle portion, the center of motion, such as the center of rotation, of the file generally corresponds with the center of the root canal. In contrast, the center of motion during cleaning of the operative middle portion is at various locations as the file is moved around the root canal.

The files used to clean the apical root portion can be designed for primarily longitudinal movement, rotational movement or combinations thereof Since it is generally not necessary to flex a file when cleaning the apical root portion as the apical root portion is typically more round than other sections of a root canal, apical root portion files need not necessarily have the same properties as the operative middle portion files in terms of flexibility, rigidity and resilience. The files used to clean the apical portion are, however, preferably sufficiently flexible to adjust to the anatomy or structure of a root canal in a manner that enables the tip of the file to reach the apex. The files also preferably have sufficient rigidity to apply pressure against the walls or surfaces of the root canal as the abrading portion of the file is urged against the walls of the root canal and simultaneously moved in a cleaning motion even after the file has moved throughout the length of the root canal. Additionally, a file configured for use in an apical root portion preferably has. adequate resilience to avoid being substantially deformed as the file passes through a root canal and also as the abrading portion is applied against the walls of the root canal. This, combination of flexibility, resilience and rigidity is provided by embodiments of PH stainless, steel file instruments according to the present invention.

A particular advantage of the use of apical portion instruments with files formed from PH stainless steel, especially a PH stainless steel such as 17-4PH that has not been hardened, is the flexibility of the file. Apical portions are often curved which can lead to ledging if the file is unable to flex. The greater flexibility of PH stainless steel files enables the file to more easily flex as compared with conventional stainless steel files. However, the PH stainless steel file is more rigid than a nickel/titanium file so that it can still effectively abrade and clean the apical portion of the root canal. In a preferred system such as is shown in FIG. 1, the files of set 10 are preferably formed from stainless steel while the files of set 40 and 70 are preferably formed from a PH stainless steel file, especially a PH stainless steel that has not been subjected to hardening or thermal aging. This preferred configuration results mainly from the high need for flexibility when moving files in the apical portion.

Files formed from PH stainless steel may have any suitable cross-section shape. FIGS. 4A–4J are transverse cross-sections of files formed from PH stainless steel that can be utilized in accordance with any methodology. When used with the preferred methodology, the file may be used to clean the operative middle portion, to improve the access to the apical root portion or to clean the apical root portion of the root canal. While these transverse cross-sections may be any section of the file, the depicted sections are taken through the abrading portion of the various files. All of the files in combination with their respective abrading portions disclosed herein are examples of means for removing and cleaning of pulp material as the file instrument is operatively moved. Additionally, each abrading portion disclosed herein is an example of a means for abrading a root canal.

Conventional file designs can also be utilized within the scope of the present invention. Accordingly, the files are not limited to the designs shown in FIGS. 4A–4J. The files preferably, however, are configured in a manner such that the potential for breakage is minimized. For example, a file with a square cross-section may be preferred over a triangular cross-section as the file with a square cross-section has a greater mass and is accordingly less likely to break. Additionally, a file configured with tines or extensions having wide angles are generally preferred over those with narrow angles. However, the preferred tine configuration depends primarily on the particular use as in some instances it is desirable to aggressively cut while in others the root can be passively cut. When it is more desirable to aggressively cut, it may be preferred for example to utilize a file with relatively narrow tines.

FIG. 4J depicts a file 310 with a generally square-shaped transverse cross-section and truncated corners 312. Abrasive grit 314 is located on truncated corners 312. Similarly such abrasive grit can be located around a file having any cross-sectional shape and be an effective abrading portion.

Figure 5:
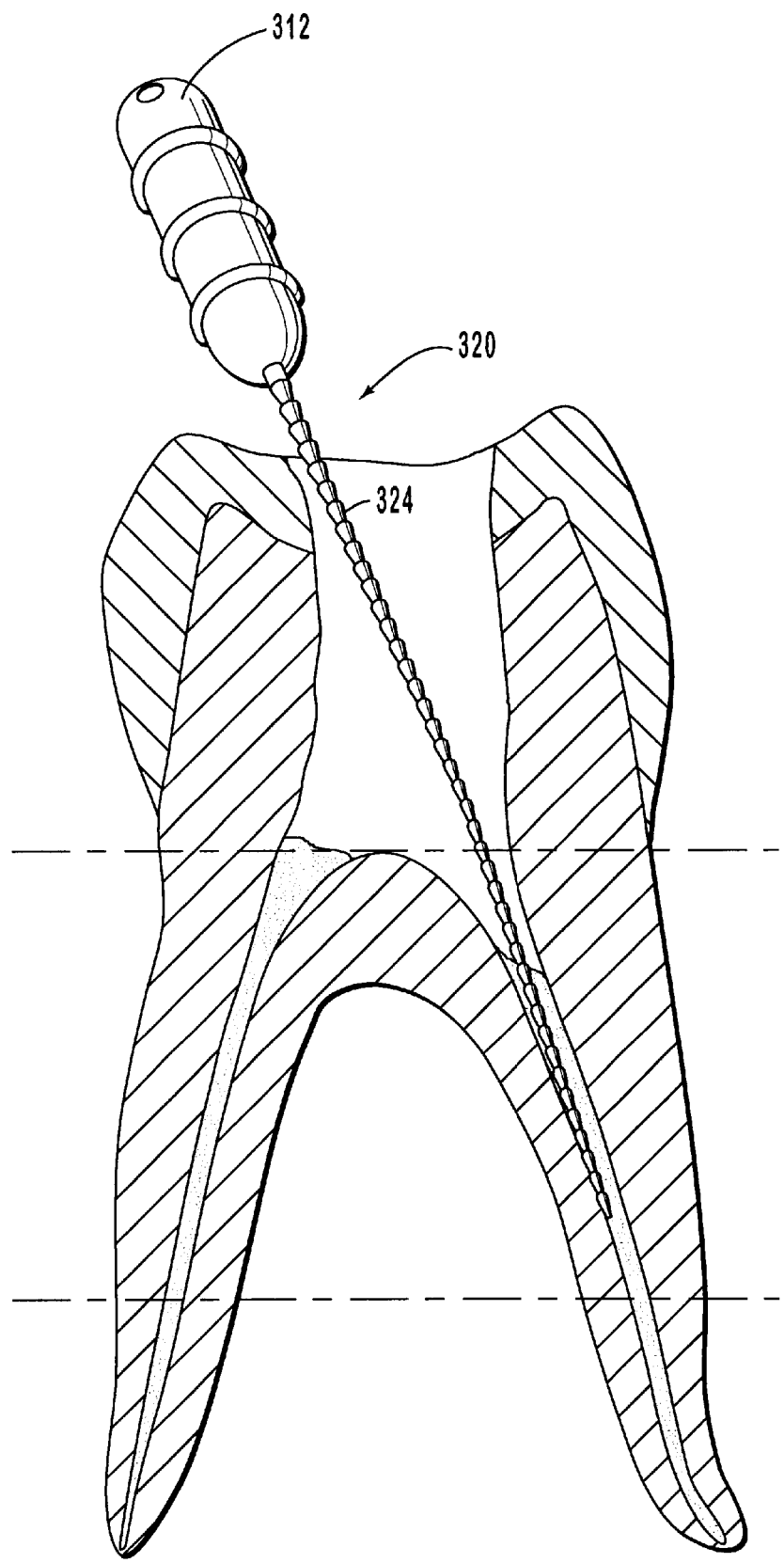
FIG. 5 is a longitudinal cross-sectional view of a tooth with a root canal being cleaned with a file instrument having a file formed by machining a groove into a metal blank.
Figure 10:
FIG. 10 is a partial perspective view of an endodontic file depicting the tip of the file.

The transverse cross-section of a file shown at FIG. 4A corresponds to the tip of a file as shown in FIG. 10A. In FIG. 5, a file instrument 320 is shown cleaning operative middle portion 160 of a root canal. Instrument 320 has a handle 322 connected to file 324 formed by machining a groove into a PH stainless steel metal blank.

Figure 6:
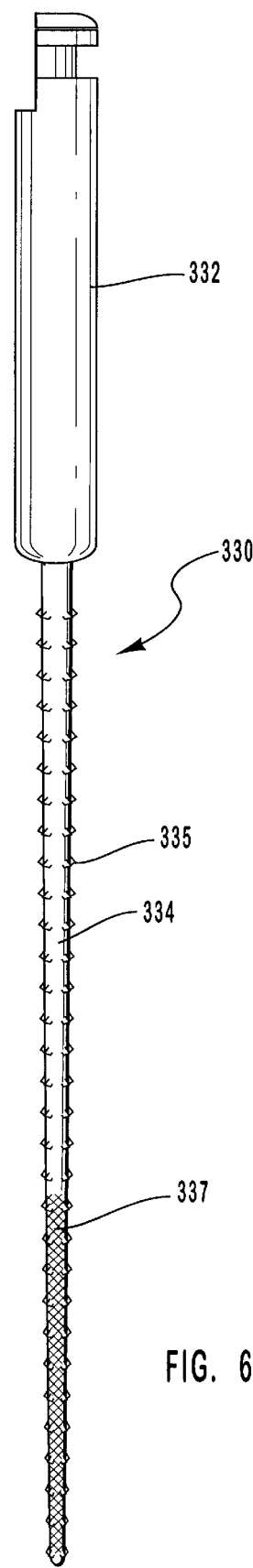
FIG. 6 is a perspective view of another embodiment of an endodontic instrument.
Figure 7:
FIG. 7 is a partial perspective view of an endodontic file depicting the tip of the file.

FIG. 6 depicts another embodiment of a file instrument shown at 330. File instrument 330 has a handle 332 which is particularly adapted for use with a mechanical instrument. The file instruments of the present invention can, however, be utilized with any suitable handle configuration. All of the handles disclosed herein are examples of end means for grasping and operatively moving a file in an abrasive action.

File instrument 330 further comprises a file 334 which is preferably used to clean the operative middle portion. File 334 has an abrading portion comprising protrusions or barbs 335 at the upper end of the file and a combination of barbs 335 and knurled surface 337 at the lower end. FIGS. 7–10 are depictions of various tips of files within the scope of the present invention.

The shapes and dimensions of the embodiments of endodontic file instruments provided herein are merely illustrative, but not limiting, of the variety of endodontic file instruments that are manufactured according to the present invention with PH stainless steels, and most preferably, with 17-4PH stainless steel.

Files comprising PH stainless steel, most preferably 17-4PH stainless steel, may be manufactured by any conventional method for manufacturing endodontic files such that the files appear like conventional K-files or Hedstrom-type files. For example, a precursor rod may be ground to cut lands into its surface such that it has a desired taper or shape. Additionally, lands may be cut into a precursor blank that with a cross-section shape that is round, triangular or square such that the file appears like file 324 shown in FIG. 5. Similarly, a blank having three or four sides may be twisted after being appropriately tapered. Files may also have protrusions or barbs such as those shown at 335 in FIG. 6. The file may also have a knurled surface as shown at 337 in FIG. 6 at the lower end. The precursor blank may also be abraded to impart a roughened surface. These conventional techniques such as twisting, cutting and appropriately machining a precursor blank to form features such as cutting surfaces, abrading surfaces or helical features with the appropriate screw periodicity can be utilized alone or in combination to manufacture PH stainless steel endodontic files.

Once the PH stainless steel endodontic file has been appropriately shaped it is then ready for use. As indicated above, conventional techniques teach that such stainless steel alloys are aged by thermal treatment to increase their hardness. However, it has been discovered in the context of the present invention that the process of manufacturing PH stainless steel endodontic files preferably does not include such a thermal aging step. Files manufactured without such a thermal aging step provide optimal characteristics for their effective use in endodontic practice.

EXAMPLES

Below are specific examples of PH stainless steel endodontic file instruments and alloys used in their manufacture according to the present invention. The following hypothetical examples are presented in order to disclose additional embodiments of the article of manufacture in the form of PH stainless steel file instruments. Examples 1–58 relate to various alloy compositions. Example 59 provides detailed information regarding a system of instruments formed from these alloy compositions.

Example 1

An embodiment of a preferred stainless steel has the following composition: up to about 0.09% C, up to about 1.00% Mn, up to about 1.00% Si, from about 14.0% to about 16.0% Cr, from about 6.5% to about 7.75% Ni, from about 2.0% to about 3.0% Mo, up to about 0.04% P, up to about 0.04% S, and from about 0.75% to about 1.50% Al.

Example 2

Another embodiment of a preferred stainless steels has the following composition: up to about 0.09% C, up to about 1.00% Mn, up to about 1.00% Si, from about 14.0% to about 16.0% Cr, from about 6.5% to about 7.75% Ni, from about 2.0% to about 3.0% Mo, up to about 0.04% P, and up to about 0.04% S.

Example 3

Another embodiment of a preferred stainless steel has the following composition: up to about 0.09% C, up to about 1.00% Mn, up to about 1.00% Si, from about 16.0% to about 18.0% Cr, from about 6.5% to about 7.75% Ni, up to about 0.04% P, up to about 0.04% S, and from about 0.75% to about 1.50% Al.

Example 4

Another embodiment of a preferred stainless steel has the following composition: from about 0.07% to about 0.11% C, from about 0.50% to about 1.25% Mn, up to about 0.50% Si, from about 16.0% to about 17.0% Cr, from about 4.0% to about 5.0% Ni, from about 2.50% to about 3.25% Mo, up to about 0.04% P, up to about 0.03% S, from about 0.07% to about 0.13% N.

Example 5

Another embodiment of a preferred stainless steel has the following composition: from about 0.07% to about 0.11% C, from about 0.50% to about 1.25% Mn, up to about 0.50% Si, from about 16.0% to about 17.0% Cr, from about 4.0% to about 5.0% Ni, from about 2.50% to about 3.25% Mo, up to 0.04% P, and up to about 0.03% S.

Example 6

Another embodiment of a preferred stainless steel has the following composition: from about 0.10% to about 0.15% C, from about 0.50% to about 1.25% Mn, up to about 0.50% Si, from about 15.0% to about 16.0% Cr, from about 4.0% to about 5.0% Ni, from about 2.50% to about 3.25% Mo, up to about 0.04% P, up to about 0.03% S, and from about 0.07% to about 0.13% N.

Example 7

Another embodiment of a preferred stainless steel has the following composition: from about 0.10% to about 0.15% C, from about 0.50% to about 1.25% Mn, up to about 0.50% Si, from about 15.0% to about 16.0% Cr, from about 4.0% to about 5.0% Ni, from about 2.50% to about 3.25% Mo, up to about 0.04% P, and up to about 0.03% S.

Example 8

Another embodiment of a preferred stainless steel has the following composition: up to about 0.08% C, up to about 2% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, from about 1.90% to about 2.35% Ti, up to about 0.35% Al, from about 0.10% to about 0.50% V, and from about 0.0030% to about 0.0100% B.

Example 9

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, from about 1.90% to about 2.35% Ti, up to about 0.35% Al, and from about 0.10% to about 0.50% V.

Example 10

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, from about 1.90% to about 2.35% Ti, up to about 0.35% Al, and from about 0.0030% to about 0.0100% B.

Example 11

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, from about 1.90% to about 2.35% Ti, from about 0.10% to about 0.50% V, and from about 0.0030% to about 0.0100% B.

Example 12

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, up to about 0.35% Al, from about 0.10% to about 0.50% V, and from about 0.0030% to about 0.0100% B.

Example 13

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, from about 1.90% to about 2.35% Ti, and up to about 0.35% Al.

Example 14

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, from about 1.90% to about 2.35% Ti, and from about 0.10% to about 0.50% V.

Example 15

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, up to about 0.35% Al, and from about 0.10% to about 0.50% V.

Example 16

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, from about 1.90% to about 2.35% Ti, and from about 0.0030% to about 0.0100% B.

Example 17

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, up to about 0.35% Al, and from about 0.0030% to about 0.0100% B.

Example 18

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, from about 0.10% to about 0.5% V, and from about 0.0030% to about 0.0100% B.

Example 19

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, and from about 1.90% to about 2.35% Ti.

Example 20

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, and up to about 0.35% Al.

Example 21

Another embodiment of a preferred stainless steel has the following composition: up to about 0.08%C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, and from about 0.10% to about 0.50% V.

Example 22

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, up to about 0.025% S, and from about 0.0030% to about 0.0100% B.

Example 23

Another embodiment of a preferred stainless steel has the following composition: up to about 0.08% C, up to about 2.00% Mn, up to about 1.00% Si, from about 13.5% to about 16.0% Cr, from about 24.0% to about 27.0% Ni, from about 1.0% to about 1.5% Mo, up to about 0.025% P, and up to about 0.025% S.

Example 24

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, up to about 0.002% S, up to about 2.15% Ti, up to about 0.25% Al, up to about 0.27% V, up to about 0.0015% B.

Example 25

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, up to about 0.002% S, up to about 2.15% Ti, up to about 0.25% Al, and up to about 0.27% V.

Example 26

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% V, up to about 0.002% S, up to about 2.15% Ti, up to about 0.25% Al, and up to about 0.0015% B.

Example 27

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, up to about 0.002% S, up to about 2.15% Ti, up to about 0.27% V, and up to about 0.0015% B.

Example 28

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, up to about 0.002% S, up to about 0.25% Al, up to about 0.27% V, and up to about 0.0015% B.

Example 29

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% B, up to about 0.002% S, up to about 2.15% Ti, and up to about 0.25% Al.

Example 30

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, up to about 0.002% S, up to about 2.15% Ti, and up to about 0.27% V.

Example 31

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, up to about 0.002% S, up to about 2.15% Ti, and up to about 0.0015% B.

Example 32

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, up to about 0.002% S, up to about 0.25% Al, and up to about 0.0015% B.

Example 33

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, up to about 0.002% S, up to about 0.27% V, and up to about 0.0015% B.

Example 34

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, up to about 0.002% S, up to about 2.15% Ti, and up to about 0.27% V.

Example 35

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, up to about 0.002% S, and up to about 0.25% Al.

Example 36

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, up to about 0.002% 5, and up to about 0.27% V.

Example 37

Another embodiment of a preferred stainless steel has the following composition: up to about 0.015% C,up to about 0.05% Mn, up to about 0.02% Si, up to about 14.5% Cr, up to about 29.5% Ni, up to about 1.25% Mo, up to about 0.006% P, up to about 0.002% S, and up to about 0.0015% B.

Example 38

Another embodiment of a preferred stainless steel has the following composition: up to about 0.015% C, up to about 0.05% Mn, up to about 0.02% Si, up to about 14.5% Cr, up to about 29.5% Ni, up to about 1.25% Mo, up to about 0.006% P, and up to about 0.002% S.

Example 39

Another embodiment of a more preferred stainless steel has the following composition: up to about 0.05% C, up to about 0.10% Mn, up to about 0.10% Si, from about 12.25% to about 13.25% Cr, from about 7.5% to about 8.5% Ni, from about 2.0% to about 2.5% Mo, up to about 0.01% P, up to about 0.008% S, from about 0.90% to about 1.35% Al, and up to about 0.1% N.

Example 40

Another embodiment of a more preferred stainless steel has the following composition: up to about 0.05% C, up to about 0.10% Mn, up to about 0.10% Si, from about 12.25% to about 13.25% Cr, from about 7.5% to about 8.5% Ni, from about 2.0% to about 2.5% Mo, up to about 0.01% P, up to about 0.008% S, and from about 0.90% to about 1.35% Al.

Example 41

Another embodiment of a more preferred stainless steel has the following composition: up to about 0.05% C, up to about 0.10% Mn, up to about 0.10% Si, from about 12.25% to about 13.25% Cr, from about 7.5% to about 8.5% Ni, from about 2.0% to about 2.5% Mo, up to about 0.01% P, up to about 0.008% S, and up to about 0.01% N.

Example 42

Another embodiment of a more preferred stainless steel has the following composition: up to about 0.05% C, up to about 0.10% Mn, up to about 0.10% Si, from about 12.25% to about 13.25% Cr, from about 7.5% to about 8.5% Ni, from about 2.0% to about 2.5% Mo, up to about 0.01% P, and up to about 0.008% S.

Example 43

Another embodiment of a more preferred stainless steel has the following composition: up to about 0.07% C, up to about 1.00% Mn, up to 1.00% Si, from about 14.0% to about 15.5% Cr, from about 3.5% to about 5.5% Ni, up to about 0.04% P, up to about 0.03% S, from about 2.5% to about 4.5% Cu, and from about 0.15% to about 0.45% Nb.

Example 44

Another embodiment of a more preferred stainless steel has the following composition: up to about 0.07% C, up to about 1.00% Mn, up to 1.00% Si, from about 14.0% to about 15.5% Cr, from about 3.5% to about 5.5% Ni, up to about 0.04% P, up to about 0.03% S, and from about 2.5% to about 4.5% Cu.

Example 45

Another embodiment of a more preferred stainless steel has the following composition: up to about 0.07% C, up to about 1.00% Mn, up to 1.00% Si, from about 14.0% to about 15.5% Cr, from about 3.5% to about 5.5% Ni, up to about 0.04% P, up to about 0.03% S, and from about 0.15% to about 0.45% Nb.

Example 46

Another embodiment of a more preferred stainless steel has the following composition: up to about 0.05% C, up to about 1.00% Mn, up to about 1.00% Si, from about 14.0% to about 16.0% Cr, from about 5.0% to about 7.0% Ni, from about 0.5% to about 1.0% Mo, up to about 0.03%, up to about 0.03% S, from about 1.25% to about 1.75% Cu, and at least about 0.4% Nb.

Example 47

Another embodiment of a more preferred stainless steel has the following composition: up to about 0.05% C, up to about 1.00% NM, up to about 1.00% Si, from about 14.0% to about 16.0% Cr, from about 5.0% to about 7.0% Ni, from about 0.5% to about 1.0% Mo, up to about 0.03% P, up to about 0.03% S, and from about 1.25% to about 1.75% Cu.

Example 48

Another embodiment of a more preferred stainless steel has the following composition: up to about 0.05% C, up to about 1.00% Mn, up to 1.00% Si, from about 14.0% to about 16.0% Cr, from about 5.0% to about 7.0% Ni, from about 0.5% to about 1.0% Mo, up to about 0.03% P, up to about 0.03% S, and at least about 0.4% Nb.

Example 49

Another embodiment of a more preferred stainless steel has the following composition: up to about 0.05% C, up to about 1.00% Mn, up to 1.00% Si, from about 14.0% to about 16.0% Cr, from about 5.0% to about 7.0% Ni, from about 0.5% to about 1.0% Mo, up to about 0.03% P, and up to about 0.03% S.

Example 50

Another embodiment of a more preferred stainless steel has the following composition: up to about 0.05% C, up to about 0.50% Mn, up to about 0.50% Si, from about 11.0% to about 12.5% Cr, from about 7.5% to about 9.5% Ni, up to about 0.50% Mo, up to about 0.04% P, up to about 0.03% S, from about 1.5% to about 2.5% Cu, from about 0.8% to about 1.4% Ti, and from about 0.1% to about 0.5% Nb.

Example 51

Another embodiment of a more preferred stainless steel has the following composition: up to about 0.05% C, up to about 0.50% Mn, up to about 0.50% Si, from about 11.0% to about 12.5% Cr, from about 7.5% to about 9.5% Ni, up to about 0.50% Mo, up to about 0.04% P, up to about 0.03% S, from about 1.5% to about 2.5% Cu, and from about 0.8% to about 1.4% Ti.

Example 52

Another embodiment of a more preferred stainless steel has the following composition: up to about 0.05% C, up to about 0.50% Mn, up to about 0.50% Si, from about 11.0% to about 12.5% Cr, from about 7.5% to about 9.5% Ni, up to about 0.50% Mo, up to about 0.04% P, up to about 0.03% S, from about 1.5% to about 2.5% Cu, and from about 0.1% to about 0.5% Nb.

Example 53

Another embodiment of a more preferred stainless steel has the following composition: up to about 0.05% C, up to about 0.50% Mn, up to about 0.50% Si, from about 11.0% to about 12.5% Cr, from about 7.5% to about 9.5% Ni, up to about 0.50% Mo, up to about 0.04% P, up to about 0.03% S, from about 0.8% to about 1.4% Ti, and from about 0.1% to about 0.5% Nb.

Example 54

Another embodiment of a more preferred stainless steel has the following composition: up to about 0.05% C, up to about 0.50% Mn, up to about 0.50% Si, from about 11.0% to about 12.5% Cr, from about 7.5% to about 9.5% Ni, up to about 0.50% Mo, up to about 0.04% P, up to about 0.03% S, and from about 1.5% to about 2.5% Cu.

Example 55

Another embodiment of a more preferred stainless steel has the following composition: up to about 0.05% C, up to about 0.50% Mn, up to about 0.50% Si, from about 11.0% to about 12.5% Cr, from about 7.5% to about 9.5% Ni, up to about 0.50% Mo, up to about 0.04% P, up to about 0.03% S, and from about 0.8% to about 1.4% Ti.

Example 56

Another embodiment of a more preferred stainless steel has the following composition: up to about 0.05% C, up to about 0.50% Mn, up to about 0.50% Si, from about 11.0% to about 12.5% Cr, from about 7.5% to about 9.5% Ni, up to about 0.50% Mo, up to about 0.04% P, up to about 0.03% S, and from about 0.1% to about 0.5% Nb.

Example 57

Another embodiment of a more preferred stainless steel has the following composition: up to about 0.05% C, up to about 0.50% Mn, up to about 0.50% Si, from about 11.0% to about 12.5% Cr, from about 7.5% to about 9.5% Ni, up to about 0.50% Mo, up to about 0.04% P, and up to about 0.03% S.

Example 58

Another embodiment of a 17-4 PH stainless steel has the following composition: up to about 0.07% C, up to about 1.00% Mn, up to about 1.00% Si, from about 15.0% to about 17.5% Cr, from about 3.0% to about 5.0% Ni, up to about 0.04% P, up to about 0.03% S, and from about 3.0% to about 5.0% Cu.

Example 59

As discussed above, FIG. 1 depicts three sets of instruments identified at 10, 40 and 70 which are used to prepare a root canal in accordance with the EndoEze® AET™ (Anatomic Endodontic Technology) of Ultradent Products, Inc. The sets of instruments identified respectively at 10, 40 and 70 are respectively used to clean the operative middle portion, to improve access into the apical portion and to clean the apical root portion. The files of each of the instruments described below may be manufactured with any of the alloy compositions described above in Examples 1–58.

Operative Middle Portion Phase and Related Sets of Instruments

Tables 1A–1D presented hereinbelow describe the dimensions of four different set of instruments which can be used to clean the operative middle portion in different teeth depending on the particular operative root canal length. These four sets are preferably sold as part of a kit. Although, the kit includes several sets of instruments, only one set of instruments is typically used for cleaning the operative middle portion. The practitioner selects from several sets in the kit depending on the particular length of the operative coronal portion and the operative middle portion. The instruments in Tables 1A–1D are designed to have a working length that is adjustable depending on the placement of a stop such as stop 140 or the position of the handle within the chuck of an endodontic handpiece. Accordingly, the working lengths for the instruments in Tables 1A–1D are respectively 15–18 mm, 19–22 mm, 23–26 mm, and 27–30 mm.

TABLE 1A

Operative Middle Portion Instruments (15–18 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 18 mm | 15 mm | 3 mm | 0.10 mm | 0.55 mm | 0.50 mm | 0.025 |
| 10b | 18 mm | 15 mm | 3 mm | 0.13 mm | 0.76 mm | 0.70 mm | 0.035 |
| 10c | 18 mm | 15 mm | 3 mm | 0.13 mm | 1.05 mm | 0.90 mm | 0.051 |
| 10d | 18 mm | 15 mm | 3 mm | 0.13 mm | 1.17 mm | 1.00 mm | 0.058 |

TABLE 1B

Operative Middle Portion Instruments (19–22 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 22 mm | 19 mm | 3 mm | 0.10 mm | 0.65 mm | 0.60 mm | 0.025 |
| 10b | 22 mm | 19 mm | 3 mm | 0.13 mm | 0.90 mm | 0.50 mm | 0.035 |
| 10c | 22 mm | 19 mm | 3 mm | 0.13 mm | 1.14 mm | 1.00 mm | 0.046 |
| 10d | 22 mm | 19 mm | 3 mm | 0.13 mm | 1.45 mm | 1.30 mm | 0.060 |

TABLE 1C

Operative Middle Portion Instruments (23–26 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 26 mm | 23 mm | 3 mm | 0.10 mm | 0.78 mm | 0.70 mm | 0.026 |
| 10b | 26 mm | 23 mm | 3 mm | 0.13 mm | 0.88 mm | 0.80 mm | 0.029 |
| 10c | 26 mm | 23 mm | 3 mm | 0.13 mm | 1.12 mm | 1.00 mm | 0.038 |
| 10d | 26 mm | 23 mm | 3 mm | 0.13 mm | 1.43 mm | 1.30 mm | 0.050 |

TABLE 1D

Operative Middle Portion Instruments (27–30 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 30 mm | 27 mm | 3 mm | 0.10 mm | 0.85 mm | 0.80 mm | 0.025 |
| 10b | 30 mm | 27 mm | 3 mm | 0.13 mm | 1.00 mm | 0.90 mm | 0.029 |
| 10c | 30 mm | 27 mm | 3 mm | 0.13 mm | 1.21 mm | 1.10 mm | 0.036 |
| 10d | 30 mm | 27 mm | 3 mm | 0.13 mm | 1.54 mm | 1.40 mm | 0.047 |

As provided in this example, the instruments having a working length of 19–22 mm as presented in Table 1B are selected for use in a tooth due to the combined length of the operative coronal portion and the operative middle portion of the operative root canal which is in the range of 19–22 mm. More particularly, the root canal of the tooth is slightly longer than about 25 mm so the full 22 mm of the working length is utilized. The set of instruments for cleaning the operative middle portion detailed in Table 1B corresponds with the set of instruments shown in FIG. 1 at 10. Since only one set of instruments is used to clean the operative middle portion only one set is shown in FIG. 1 at 10.

When utilized to clean the operative middle portion of a root canal, file 10a is first introduced into the operative middle portion followed by file instrument 10b, 10c and then 10d. Note that, as shown in FIG. 1, the diameter at the top of each abrading portion 19a–d is incrementally greater than the diameter of the top of the abrading portion of the preceding file. Accordingly, the diameter of the top end of each successive file introduced into the operative middle portion is greater than the diameter of the top end of each preceding file. However, the tip diameter of each file in set of operative middle portion instruments are essentially the same. More particularly, the instruments in each set detailed above has a first instrument 10a with a tip diameter of 0.10 mm while the instruments sequentially used thereafter have a tip diameter of either 0.13 mm.

Since the tip diameters are essentially equal and since the diameter of the top end of each successive file introduced into the operative middle portion is larger than the diameter of the top end of the preceding file, the taper of each successive file in the set is larger than the preceding file as shown in Tables 1A–1D. Each successive file accordingly has an increased surface area for cleaning the root canal. Additionally, as files are inserted into a root canal with larger and larger tapers, the rigidity of the upper half of each successive file also increases. The increase in rigidity is, however, minimized by maintaining the tip of each file at about the same diameter. The flexibility of the lower half remains essentially constant. The rigidity in the upper half is used to remove interferences and to properly rectify the operative coronal portion 260 and the operative middle portion 262. The consistency in rigidity at the upper half is useful since the lateral perimetrical force applied to the handle is prey transferred to its upper half or at least the part closest to the handle, which is the strongest part of the file.

By properly selecting a combination of factors including the diameters of the files at the top ends and at the tips as well as the material used to form the files, the files are designed such that each file has sufficient flexibility to be flexed or curved to urge the abrading portion against the surfaces or walls of the root canal and sufficient rigidity to apply pressure against the surfaces of the root canal as the abrading portion of the file is urged against the surfaces of the root canal and simultaneously moved in a cleaning motion. Accordingly, a practitioner can move the instrument around the perimeter of the operative middle portion of the root canal using the contours of the operative middle portion as a guide for the movement of the instrument such that the original anatomy is enlarged and not significantly altered.

The operative middle portion instruments in each set are preferably formed from stainless steel.

The operative middle portion instruments in each set may be formed from stainless steel and used in conjunction with a set of apical portion instruments formed from PH stainless steel that has preferably not been heat treated. The operative middle portion instruments may also be formed from any PH stainless steel alloy such as those described in Examples 1–58, that has preferably not been heat treated.

Apical Portion Widening Phase and Related Sets of Instruments

Tables 2A–2C detail the dimensions of instruments with file lengths which are respectively 21 mm, 25 mm and 30 mm. In this example, the set presented in Table 2B is a selected since a tooth is being instrumented with a root canal that is slightly longer than about 25 mm. The set presented in Table 2B is shown in FIG. 1 as set 40.

TABLE 2A

Apical Widening Instruments (21 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 40a | 21 mm | 5 mm | 11 mm | 5 mm | 0.08 mm | 0.28 mm | 0.30 mm | 0.80 mm | 0.04 |
| 40b | 21 mm | 5 mm | 11 mm | 5 mm | 0.08 mm | 0.38 mm | 0.40 mm | 1.1 mm | 0.06 |

TABLE 2B

Apical Widening Instruments (25 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 40a | 25 mm | 5 mm | 15 mm | 5 mm | 0.08 mm | 0.28 mm | 0.30 mm | 0.90 mm | 0.04 |
| 40b | 25 mm | 5 mm | 15 mm | 5 mm | 0.08 mm | 0.38 mm | 0.40 mm | 1.3 mm | 0.06 |

TABLE 2C

Apical Widening Instruments (30 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 40a | 30 mm | 5 mm | 20 mm | 5 mm | 0.08 mm | 0.28 mm | 0.30 mm | 1.1 mm | 0.04 |
| 40b | 30 mm | 5 mm | 20 mm | 5 mm | 0.08 mm | 0.38 mm | 0.40 mm | 1.6 mm | 0.06 |

The files of the instruments in the sets detailed in Tables 2A–2C may be formed from any PH stainless steel alloy such as those described in Examples 1–58, that has preferably not been heat treated. Each file has three sections including a smooth shank portion, a square portion and an abrading portion. As indicated above, the set presented in Table 2B corresponds with set 40 shown in FIG. 1. Note, however, with the exception of length, the instruments detailed in Table 2A and Table 2C would appear just like set 40. Instrument 40a has a file 44a with smooth shank portion 46a, a square portion 47a, an abrading portion 49a and a file tip 48a As shown, the smooth shank portion 46a is the top section of file 44a and a handle 42 is positioned on shank portion 46a. Smooth shank portion 46a tapers to square portion 47a which is between shank portion 46a and abrading portion 49a.

The smooth shank portion enables stops be positioned on the file to adjust the working length of the file. Each smooth shank portion of each file has a length of about 5 mm with various diameters. The instruments can be used for all operative lengths that are likely to be encountered in clinical practice through the positioning of the stops at the predetermined lengths. While the instruments can be offered in a more expanded series of millimetrically different lengths, the use of stops is acceptable, particularly since, these instruments are manually moved.

In each set, the diameter at the top of the square portion of instrument number 40a and instrument number 40b is respectively 0.30 mm and 0.40 mm. The abrading portion is formed by twisting the square section so that the abrading portion has a K-file configuration. The instruments in each set all have the same tip diameters. The taper of the files from the tip ($D_1$) to the diameter at the top of the square portion ($D_3$) remains constant and is respectively 0.04 and 0.06 for instrument number 40a and instrument number 40b in each set.

Preferably, instrument 40a is first utilized and then instrument 40b to obtain, in a gradual manner, the desired enlargement of the specific transition zone between the operative middle portion and the apical portion. This enlargement is also preferably achieved without significantly changing the diameter of the apical portion of the canal. Accordingly, the tip diameter ($D_1$) of the various instruments in this set remains constant while the diameter at the top of the cutting area or abrading portion ($D_2$), located 5 mm from the tip, is graduated from one instrument to the next, reaching a maximum diameter of 0.38 mm. The rest of the shaft, up to the handle, does not have a cutting surface. To the extent that these instruments are used to expand the apical portion of the canal, the practitioner should constantly bear in mind the average diameters of the canals and the average thicknesses of the parietal walls at the apex.

The advantage of using PH stainless steel that has preferably not been heat treated to manufacture the files of this optional set is that they are flexible enough to negotiate the curves of the apical portion without ledging. Also, since they are more rigid than Ni/Ti files they are able to abrade the transition into the apical portion as needed.

Note that the entire length of each file can be configured with an abrading portion, however, each abrading portion 49a–b preferably extends from tip 48a–b along only some of the file. Accordingly, the abrading portion may have any suitable length such as 3 mm or 10 mm; however, the abrading portion in a preferred configuration is about 5 mm or about 6 mm.

As indicated above, the length of a file such as files 44a–b is preferably sufficiently such that when the file is inserted into the root canal, the tip can at least approximately reach the apex and the abrading portion 49a–b of the file can improve the access into the apical portion of the root canal. Although files used to improve the access into the apical root portion may be long enough to approximately reach the apex, the files can be used to improve the access as long as the files can reach the bottom of the operative middle portion and the top of the apical root portion. Such file lengths are typically within a range from about 8 mm to about 35 mm, more typically in a range from about 14 mm to about 35 mm and most typically in a range from about 12 mm to about 33 mm. The length of the abrading portion is generally within a range from about 1 mm to about 35 mm, more preferably in a range from about 2 mm to about 16 mm and most preferably in a range from about 3 mm to about 6 mm. The abrading portion is preferably long enough so that the entire apical portion can be abraded as well as at least the bottom of the operative middle portion.

In a set of instruments used to improve the access into an apical root portion, the file tips of the instruments preferably all have about the same diameter as shown in Tables 2A–2C and in FIG. 1 at 48a–b. The diameter of the tips may range from about 0.06 mm to about 1 mm, however, the tips preferably have a diameter of about 0.08 mm. In a less preferred embodiment, the tip diameter of each file may also increase sequentially.

As shown in Tables 2A–2C and in FIG. 1, the diameter of the abrading portions 49a–b increases from the tips 48a–b towards the top of the abrading portions. The diameter of the abrading portion at the top may range from about 0.1 mm to about 0.4 mm and is more preferably in a range from about 0.2 mmn to about 0.4 mm Each successive file has an abrading portion, 49a–49b which is successively larger in diameter at the top of the abrading portion than the abrading portion of the preceding file. Accordingly, a set may have files with abrading portions having the following respective top diameters: about 0.2 mm, about 0.25 mm, about 0.3 mm and about 0.35 mm. Each abrading portion in such a set has a different taper. Note that the taper of the smooth or shank portions above the abrading portions also increases sequentially, however, the taper may also remain essentially the same.

Apical Portion Cleaning Phase and Related Sets of Instruments

Again sets of instruments are provided with each set having a different length. Three sets of instruments are described hereinbelow which are designed for removing and cleaning essentially all pulp material from the apical root portion after access into the apical root portion has been improved by a set of instruments such as set 40 detailed in Table 2B. In some instances, the instruments described in this example can also be used to clean the pulp material from the root canal immediately after the operative middle portion has been cleaned by a set of instruments such as the sets presented in Table 1B.

Tables 3A–3C detail the dimensions of instruments with file lengths which are respectively 21 mm, 25 mm and 30 mm. However, please note that only instruments from Table 3B are used in the tooth being cleaned in this example. The set of instruments detailed in Table 3B are shown in FIG. 1 as set 70. Set 70 includes instruments 70a–l which respectively correspond with instruments 70a–l in the set presented in Table 3B.

The instruments in set 70 have a similar appearance as the instruments in set 40. Instruments 70a–l have a handle 72 opposite a file 74. Each file 74 has a smooth shank portion 76, a square portion 77, an abrading portion 79 and a file tip 78. The sets of instruments presented in Table 3A and 3C have a similar appearance to instruments detailed in Table 3B and shown at 70, however, the files have different lengths. The taper of the files from the tip ($D_1$) to the diameter at the top of the square portion ($D_3$) is provided in each table.

TABLE 3A

Apical Cleaning Instruments (21 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 70a | 21 mm | 5 mm | 11 mm | 5 mm | 0.10 mm | 0.20 mm | 0.42 mm | 0.50 mm | 0.02 |
| 70b | 21 mm | 5 mm | 11 mm | 5 mm | 0.15 mm | 0.25 mm | 0.47 mm | 0.50 mm | 0.02 |
| 70c | 21 mm | 5 mm | 11 mm | 5 mm | 0.20 mm | 0.30 mm | 0.52 mm | 0.60 mm | 0.02 |
| 70d | 21 mm | 5 mm | 11 mm | 5 mm | 0.25 mm | 0.375 mm | 0.65 mm | 0.70 mm | 0.025 |
| 70e | 21 mm | 5 mm | 11 mm | 5 mm | 0.30 mm | 0.425 mm | 0.70 mm | 0.70 mm | 0.025 |
| 70f | 21 mm | 5 mm | 11 mm | 5 mm | 0.35 mm | 0.475 mm | 0.75 mm | 0.80 mm | 0.025 |
| 70g | 21 mm | 5 mm | 11 mm | 5 mm | 0.40 mm | 0.525 mm | 0.80 mm | 0.80 mm | 0.025 |
| 70h | 21 mm | 5 mm | 11 mm | 5 mm | 0.50 mm | 0.625 mm | 0.90 mm | 0.90 mm | 0.025 |
| 70i | 21 mm | 5 mm | 11 mm | 5 mm | 0.60 mm | 0.725 mm | 1.0 mm | 1.0 mm | 0.025 |
| 70j | 21 mm | 5 mm | 11 mm | 5 mm | 0.70 mm | 0.825 mm | 1.1 mm | 1.1 mm | 0.025 |
| 70k | 21 mm | 5 mm | 11 mm | 5 mm | 0.80 mm | 0.925 mm | 1.2 mm | 1.2 mm | 0.025 |
| 70l | 21 mm | 5 mm | 11 mm | 5 mm | 1.0 mm | 1.125 mm | 1.4 mm | 1.5 mm | 0.025 |

TABLE 3B

Apical Cleaning Instruments (25 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 70a | 25 mm | 5 mm | 15 mm | 5 mm | 0.10 mm | 0.20 mm | 0.50 mm | 0.50 mm | 0.02 |
| 70b | 25 mm | 5 mm | 15 mm | 5 mm | 0.15 mm | 0.25 mm | 0.55 mm | 0.60 mm | 0.02 |
| 70c | 25 mm | 5 mm | 15 mm | 5 mm | 0.20 mm | 0.30 mm | 0.60 mm | 0.60 mm | 0.02 |
| 70d | 25 mm | 5 mm | 15 mm | 5 mm | 0.25 mm | 0.375 mm | 0.75 mm | 0.80 mm | 0.025 |
| 70e | 25 mm | 5 mm | 15 mm | 5 mm | 0.30 mm | 0.425 mm | 0.80 mm | 0.80 mm | 0.025 |
| 70f | 25 mm | 5 mm | 15 mm | 5 mm | 0.35 mm | 0.475 mm | 0.85 mm | 0.90 mm | 0.025 |
| 70g | 25 mm | 5 mm | 15 mm | 5 mm | 0.40 mm | 0.525 mm | 0.90 mm | 0.90 mm | 0.025 |
| 70h | 25 mm | 5 mm | 15 mm | 5 mm | 0.50 mm | 0.625 mm | 1.0 mm | 1.0 mm | 0.025 |
| 70i | 25 mm | 5 mm | 15 mm | 5 mm | 0.60 mm | 0.725 mm | 1.1 mm | 1.1 mm | 0.025 |
| 70j | 25 mm | 5 mm | 15 mm | 5 mm | 0.70 mm | 0.825 mm | 1.2 mm | 1.2 mm | 0.025 |
| 70k | 25 mm | 5 mm | 15 mm | 5 mm | 0.80 mm | 0.925 mm | 1.3 mm | 1.3 mm | 0.025 |
| 70l | 25 mm | 5 mm | 15 mm | 5 mm | 1.0 mm | 1.125 mm | 1.5 mm | 1.5 mm | 0.025 |

TABLE 3C

Apical Cleaning Instruments (30 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 70a | 30 mm | 5 mm | 20 mm | 5 mm | 0.10 mm | .20 mm | 0.60 mm | 0.60 mm | 0.02 |
| 70b | 30 mm | 5 mm | 20 mm | 5 mm | 0.15 mm | 0.25 mm | 0.65 mm | 0.70 mm | 0.02 |
| 70c | 30 mm | 5 mm | 20 mm | 5 mm | 0.20 mm | 0.30 mm | 0.70 mm | 0.70 mm | 0.02 |
| 70d | 30 mm | 5 mm | 20 mm | 5 mm | 0.25 mm | 0.375 mm | 0.875 mm | 0.90 mm | 0.025 |
| 70e | 30 mm | 5 mm | 20 mm | 5 mm | 0.30 mm | 0.425 mm | 0.925 mm | 1.0 mm | 0.025 |
| 70f | 30 mm | 5 mm | 20 mm | 5 mm | 0.35 mm | 0.475 mm | 0.975 mm | 1.0 mm | 0.025 |
| 70g | 30 mm | 5 mm | 20 mm | 5 mm | 0.40 mm | 0.525 mm | 1.025 mm | 1.1 mm | 0.025 |
| 70h | 30 mm | 5 mm | 20 mm | 5 mm | 0.50 mm | 0.625 mm | 1.125 mm | 1.2 mm | 0.025 |
| 70i | 30 mm | 5 mm | 20 mm | 5 mm | 0.60 mm | 0.725 mm | 1.225 mm | 1.3 mm | 0.025 |
| 70j | 30 mm | 5 mm | 20 mm | 5 mm | 0.70 mm | 0.825 mm | 1.325 mm | 1.4 mm | 0.025 |
| 70k | 30 mm | 5 mm | 20 mm | 5 mm | 0.80 mm | 0.925 mm | 1.425 mm | 1.5 mm | 0.025 |
| 70l | 30 mm | 5 mm | 20 mm | 5 mm | 1.0 mm | 1.125 mm | 1.625 mm | 1.7 mm | 0.025 |

After the apical portion has been properly widened, the practitioner selects a set of files having the appropriate length, such as one of the sets presented in Tables 3A–3C. To ensure that the files have an appropriate working length, it may be necessary to place stops around the shank portions of the files identified for example at 76. The practitioner then selects an instrument from the set identified as having an appropriate length for introduction into the root canal down to the apical portion.

As indicated above, in this example, an instrument is selected from the set detailed in Table 3B, which is shown in FIG. 1 as set 70. After selecting an instrument, the practitioner then determines, based on feel and experience, whether the file is appropriately sized or whether a larger or smaller file is needed. For instance, if the practitioner selects instrument number 70b from the set detailed in Table 3B and shown in FIG. 1 at 70b which has a tip diameter of 0.15 mm and the file binds after insertion, then the practitioner would switch to instrument number 70a which has a tip diameter of 0.10 mm. Similarly, if instrument number 70b is too loose then the practitioner would then switch to instrument number 70c which has a tip diameter of 0.20 mm. The practitioner then uses that appropriately sized instrument to clean the apical portion of the root canal by hand. If the practitioner concludes after using an appropriately sized file, that further instrumentation is still needed within the apical portion then the instrument with the next largest file may be used. It is typically unnecessary to use a third instrument with an even larger file after using a series of two instruments. However, the practitioner may clean the apical root portion with a series of more than two instruments as deemed necessary by the practitioner in order to fully clean the apical portion.

Each file 74 of the file instruments designed for cleaning the apical root portion of a root canal is configured to have an abrading portion 79 along at least a portion of the length of file 74. The entire length of each file 74 can be configured with an abrading portion 79, however, abrading portion 79 preferably extends from tip 78 part way upward towards the top end of the file such that the remainder of file 74 is relatively smooth. More particularly, each file is preferably configured with an abrading portion along less than about half of the length of the file and more preferably about one-third of the length between tip 78 and the top end of the file. The abrading portion 79 can have a similar or identical configuration to the abrading portion of the file or files used to clean the operative middle portion of the root canal or the files used to improve the access into the apical root portion.

The length of a file such as apical portion files is sufficient such that when the files are inserted into the root canal the tips can at least approximately reach the apex and the abrading portion of the files can substantially contact and clean the pulp material in the apical portion of the root canal. Such file lengths are generally within a range from about 8 mm to about 35 mm, more typically in a range from about 14 mm to about 35 mm and most typically in a range from about 12 mm to about 33 mm The length of the abrading portion is generally within a range from about 1 mm to about 35 mm, more preferably in a range from about 2 mm to about 16 mm and most preferably in a range from about 3 mm to about 6 mm.

The diameter of the abrading portion is generally within a range from about 0.06 mm to about 1.4 mm. As shown in FIG. 1, each successive file has an abrading portion, identified as 79a–l, which is successively larger in diameter at the top of the abrading portion than the abrading portion of the preceding file.

The diameter of the tips 78a–c of each file may be increased incrementally such that each sequentially utilized cleaning instrument has a slightly larger tip diameter than the preceding instrument or the tip diameters may be about equal in diameter.

Additionally, the taper of files 74a–l from tip 78a–l to the top end of the abrading portion may be the same. The taper may also increase from file to file. The diameter at the top end of the file is preferably greater than the diameter of the abrading portion ash shown in Tables 3A–3C. However, the diameter at the top end of the file can also be equal to or less than the diameter of the abrading portions or even the tip in some embodiments.

The abrading portion 79 of each file 74 of file instruments 70a–l are preferably formed by twisting a blank so as to form a spiral. However, as discussed above, the blank may be shaped by any suitable method. The abrading portion 79 preferably has few spirals such that the action of abrading portion 79 against the walls or surfaces of the apical portion of the root canal is relatively gentle. Such an abrading portion is less aggressive as fewer spirals results in tines that have a wider angle.

Set 10 and set 40 are preferably disposed after use. However, since only one or two instruments from set 70 are used, it is preferable to replace or clean the instruments used from set 70. All of the sets of instruments described in this example may be sold together as a comprehensive kit or various sets may be grouped together as kits intended for use with teeth of particular lengths. For example, the sets used in the tooth cleaned in this example which are detailed in Table 1B, 2B and 3B may be sold together. Additionally, since set 10 and set 40 are intended to be single use sets these sets may also be sold together as a single use disposable kit.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An endodontic file sized for insertion into a root canal, and adapted for abrasive action in the root canal, the endodontic file comprising a PH stainless steel that has not been heat treated such that its flexibility remains unaltered after it is formed in order to enable the endodontic file to optimally flex in the root canal.

2. The endodontic file as recited in claim 1, wherein said PH stainless steel is a martensitic precipitation hardenable stainless steel.

3. The endodontic file as recited in claim 1, wherein said PH stainless steel is a semiaustenitic precipitation hardenable stainless steel.

4. The endodontic file as recited in claim 1, wherein said PH stainless steel is an austenitic precipitation hardenable stainless steel.

5. The endodontic file as recited in claim 1, wherein said PH stainless steel is 17-4PH stainless steel.

6. The endodontic file as recited in claim 1, wherein said PH stainless steel is 17-7PH stainless steel.

7. The endodontic file as recited in claim 1, wherein said PH stainless steel is selected from the group consisting of PH15-7Mo stainless steel, AM-350 stainless steel, and M-355 stainless steel.

8. The endodontic file as recited in claim 1, wherein said PH stainless steel is selected from the group consisting of A-286 stainless steel, and JBK-75(b) stainless steel.

9. The endodontic file as recited in claim 1, wherein said PH stainless steel is selected from the group consisting of PH13-8Mo stainless steel, 15-5PH stainless steel, Custom 450, and Custom 455 stainless steel.

10. The endodontic file as recited in claim 1, wherein said PH stainless steel comprises from about 10% to about 20% Cr, and from about 2% to about 35% Ni.

11. The endodontic file as recited in claim 1, wherein said PH stainless steel comprises from about 12% to about 18% Cr, and from about 2% to about 20% Ni.

12. The endodontic file as recited in claim 1, wherein said PH stainless steel comprises from about 12% to about 18% Cr, and from about 3% to about 10% Ni.

13. The endodontic file as recited in claim 1, wherein said PH stainless steel comprises from about 14% to about 18% Cr, and from about 2.5% to about 6% Ni.

14. The endodontic file as recited in claim 1, wherein said PH stainless steel comprises from about 10% to about 20% Cr, from about 2% to about 35% Ni, and at least one of the following constituents: up to about 2.2% Mn, up to about 1.2% Si, up to about 3.5% Mo, up to about 0.05% P, up to about 0.05% S, up to about 5% Cu, up to about 1.6% Al, up to about 1% Nb, up to about 2.5% Ti, up to about 0.5% V, up to about 0.2% C, up to about 0.15% N, and up to about 0.01% B.

15. The endodontic file as recited in claim 1, wherein said PH stainless steel comprises from about 10% to about 20% Cr, from about 2% to about 35% Ni, and at least one of the following constituents: up to about 2.2% Mn, up to about 1.2% Si, up to about 3.5% Mo, up to about 0.05% P, up to about 0.05% S, up to about 5% Cu, up to about 1.6% Al, at least about 0.4% Nb, up to about 2.5% Ti, up to about 0.5% V, up to about 0.2% C, up to about 0.15% N, and up to about 0.01% B.

16. The endodontic file as recited in claim 1, wherein said PH stainless steel comprises from about 10% to about 20% Cr, from about 2% to about 35% Ni, up to about 0.2% C, up to about 2.2% Mn, up to about 1.2% Si, up to about 0.05% P, up to about 0.05% S, and at least one of the following constituents: up to about 3.5% Mo, up to about 5%, Cu, up to about 1.6% Al, up to about 1% Nb, up to about 2.5% Ti, up to about 0.5% V, up to about 0.15% N, and up to about 0.01% B.

17. The endodontic file as recited in claim 1, wherein said PH stainless steel comprises from about 10% to about 20% Cr, from about 2% to about 35% Ni, up to about 0.2% C, up to about 2.2% Mn, up to about 1.2% Si, up to about 0.05% P, up to about 0.05% S, and at least one of the following constituents: up to about 3.5% Mo, up to about 5% Cu, up to about 1.6% Al, at least about 0.4% Nb, up to about 2.5% Ti, up to about 0.5% V, up to about 0.15% N, and up to about 0.01% B.

18. The endodontic file as recited in claim 1, wherein said PH stainless steel comprises from about 12% to about 18% Cr, from about 2% to about 20% Ni, and at least one of the following constituents: up to about 2.2% Mn, up to about 1.2% Si, up to about 3.5% Mo, up to about 0.05% P, up to about 0.05% S, up to about 5% Cu, up to about 1.6% Al, up to about 1% Nb, up to about 2.5% Ti, up to about 0.5% V, up to about 0.2% C, up to about 0.15% N, and up to about 0.01% B.

19. The endodontic file as recited in claim 1, wherein said PH stainless steel comprises from about 12% to about 18% Cr, from about 2% to about 20% Ni, and at least one of the following constituents: up to about 2.2% Mn, up to about 1.2% Si, up to about 3.5% Mo, up to about 0.05% P, up to about 0.05% S, up to about 5% Cu, up to about 1.6% Al, at least about 0.4% Nb, up to about 2.5% Ti, up to about 0.5% V, up to about 0.2% C, up to about 0.15% N, and up to about 0.01% B.

20. The endodontic file as recited in claim 1, wherein said PH stainless steel comprises from about 12% to about 18% Cr, from about 2% to about 20% Ni, up to about 0.2% C, up to about 2.2% Mn, up to about 1.2% Si, up to about 0.05% P, up to about 0.05% S, and at least one of the following constituents: up to about 3.5% Mo, up to about 5% Cu, up to about 1.6% Al, up to about 1% Nb, up to about 2.5% Ti, up to about 0.5% V, up to about 0.15% N, and up to about 0.01% B.

21. The endodontic file as recited in claim 1, wherein said PH stainless steel comprises from about 12% to about 18% Cr, from about 2% to about 20% Ni, up to about 0.2% C, up to about 2.2% Mn, up to about 1.2% Si, up to about 0.05% P, up to about 0.05% S, and at least one of the following constituents: up to about 3.5% Mo, up to about 5% Cu, up to about 1.6% Al, at least about 0.4% Nb, up to about 2.5% Ti, up to about 0.5% V, up to about 0.15% N, and up to about 0.01% B.

22. The endodontic file as recited in claim 1, wherein said PH stainless steel comprises from about 12% to about 18% Cr, from about 3% to about 10% Ni, and at least one of the following constituents: up to about 2.2% Mn, up to about 1.2% Si, up to about 3.5% Mo, up to about 0.05% P, up to about 0.05% S, up to about 5% Cu, up to about 1.6% Al, up to about 1% Nb, up to about 2.5% Ti, up to about 0.5% V, up to about 0.2% C, up to about 0.15% N, and up to about 0.01% B.

23. The endodontic file as recited in claim 1, wherein said PH stainless steel comprises from about 12% to about 18% Cr, from about 3% to about 10% Ni, and at least one of the following constituents: up to about 2.2% Mn, up to about 1.2% Si, up to about 3.5% Mo, up to about 0.05% P, up to about 0.05% S, up to about 5% Cu, up to about 1.6% Al, at least about 0.4% Nb, up to about 2.5% Ti, up to about 0.5% V, up to about 0.2% C, up to about 0.15% N, and up to about 0.01% B.

24. The endodontic file as recited in claim 1, wherein said PH stainless steel comprises from about 12% to about 18% Cr, from about 3% to about 10% Ni, up to about 0.2% C, up to about 2.2% Mn, up to about 1.2% Si, up to about 0.05% P, up to about 0.05% S, and at least one of the following constituents: up to about 3.5% Mo, up to about 5% Cu, up to about 1.6% Al, up to about 1% Nb, up to about 2.5% Ti, up to about 0.5% V, up to about 0.15% N, and up to about 0.01% B.

25. The endodontic file as recited in claim 1, wherein said PH stainless steel comprises from about 12% to about 18% Cr, from about 3% to about 10% Ni, up to about 0.2% C, up to about 2.2% Mn, up to about 1.2% Si, up to about 0.05% P, up to about 0.05% S, and at least one of the following constituents: up to about 3.5% Mo, up to about 5% Cu, up to about 1.6% Al, at least about 0.4% Nb, up to about 2.5% Ti, up to about 0.5% V, up to about 0.15% N, and up to about 0.01% B.

26. The endodontic file as recited in claim 1, wherein said PH stainless steel comprises from about 4% to about 18% Cr, from about 2.5% to about 6% Ni, and at least one of the following constituents: up to about 2.2% Mn, up to about 1.2% Si, up to about 3.5% Mo, up to about 0.05% P, up to about 0.05% S, up to about 5% Cu, up to about 1.6% Al, up to about 1% Nb, up to about 2.5% Ti, up to about 0.5% V, up to about 0.2% C, up to about 0.15% N, and up to about 0.01% B.

27. The endodontic file as recited in claim 1, wherein said PH stainless steel comprises from about 4% to about 18% Cr, from about 2.5% to about 6% Ni, and at least one of the following constituents: up to about 2.2% Mn, up to about 1.2% Si, up to about 3.5% Mo, up to about 0.05% P, up to about 0.05% S, up to about 5% Cu, up to about 1.6% Al, at least about 0.4% Nb, up to about 2.5% Ti, up to about 0.5% V, up to about 0.2% C, up to about 0.15% N, and up to about 0.01% B.

28. The endodontic file as recited in claim 1, wherein said PH stainless steel comprises from about 4% to about 18% Cr, from about 2.5% to about 6% Ni, up to about 0.2% C, up to about 2.2% Mn, up to about 1.2% Si, up to about 0.05% P, up to about 0.05% S, and at least one of the following constituents: up to about 3.5% Mo, up to about 5%

Cu. up to about 1.6% Al, up to about 1% Nb, up to about 2.5% Ti, up to about 0.5% V, up to about 0.15% N, and up to about 0.01% B.

29. The endodontic file as recited in claim 1, wherein said PH stainless steel comprises from about 4% to about 18% Cr, from about 2.5% to about 6% Ni, up to about 0.2% C, up to about 2.2% Mn, up to about 1.2% Si, up to about 0.05% P, up to about 0.05% S, and at least one of the following constituents: up to about 3.5% Mo, up to about 5% Cu, up to about 1.6% Al, at least about 0.4% Nb, up to about 2.5% Ti, up to about 0.5% V, up to about 0.15% N, and up to about 0.01% B.

30. The endodontic file as recited in claim 1, wherein said PH stainless steel comprises from about 15.0% to about 17.5% Cr, from about 3.0% to about 5.0% Ni, up to about 0.07% C, up to about 1.00% Mn, up to about 1.00% Si, up to about 0.04% P, up to about 0.03% S, from about 3.0% to about 5.0% Cu, and from about 0.15% to about 0.45% Nb.

31. The endodontic file as recited in claim 1, wherein said PH stainless steel comprises from about 15.0% to about 17.5% Cr, from about 3.0% to about 5.0% Ni, up to about 0.07% C, up to about 1.00% Mn, up to about 1.00% Si, up to about 0.04% P, up to about 0.03% S, and from about 0.15% to about 0.45% Nb.

32. An endodontic file is sized for insertion into a root canal, and adapted for abrasive action in the root canal, the endodontic file comprising a 17-4PH stainless steel that has not been heat treated such that its flexibility remains unaltered after it is formed in order to enable the endodontic file to optimally flex in the root canal.

33. A method of manufacturing a stainless steel endodontic file instrument which has an operative middle portion file comprising:

(a) providing a precursor blank having a proximal end and a distal end;

(b) forming the precursor blank into a file that is sized for insertion into a root canal, and that is adapted for abrasive action in the root canal, the precursor blank comprising a PH stainless steel that has not been heat treated such that the flexibility of the PH stainless steel precursor blank remains unaltered after it is formed in order to enable the endodontic file to optimally flex in the root canal.

34. The method of manufacturing a stainless steel file instrument as recited in claim 33, wherein the file is formed from the PH stainless steel precursor blank by cutting lands into the precursor blank.

35. The method of manufacturing a stainless steel file instrument as recited in claim 33, wherein the file is formed from the PH stainless steel precursor blank by twisting the precursor blank.

* * * * *

UNITED STATES PATENT AND TRADEMARK OFFICE
CERTIFICATE OF CORRECTION

PATENT NO.     : 6,514,076 B1
DATED          : February 4, 2003
INVENTOR(S)    : Bleiweiss et al.

It is certified that error appears in the above-identified patent and that said Letters Patent is hereby corrected as shown below:

Column 1,
Line 36, after "thereof" please insert -- . --

Column 4,
Line 9, please change "edging." to -- ledging. --

Column 5,
Line 53, after "precursor blank by" please change "an" to -- a --
Line 57, after "and combinations thereof" please insert -- . --

Column 8,
Line 10, after "International" please insert -- , --
Line 40, after "in providing" please change "composition al" to -- compositional --

Column 9,
Line 52, after "application Ser. No." please remove "3"

Column 10,
Line 38, after "used to clean" please remove the second instance of "to clean"
Line 44, after "to use an" please change "instruments" to -- instrument --

Column 11,
Line 25, after "portion 260 before" please delete "the"

Column 13,
Line 56, after "followed by" please change "then" to -- the --

Column 14,
Line 40, after "combinations thereof" please insert -- . --
Line 56, after "has" please insert -- . --
Line 59, after "canal. This" please remove ","
Line 60, after "embodiments of PH stainless" please remove ","

Column 21,
Line 28, after "up to about 0.002%" please change "5" -- S --
Line 32, after "0.015% C" please change "C,up" to -- C, up --

UNITED STATES PATENT AND TRADEMARK OFFICE
CERTIFICATE OF CORRECTION

PATENT NO. : 6,514,076 B1
DATED : February 4, 2003
INVENTOR(S) : Bleiweiss et al.

It is certified that error appears in the above-identified patent and that said Letters Patent is hereby corrected as shown below:

Column 22,
Line 44, after "up to about 0.03%" please insert -- P --
Line 52, after "about 1.00%" please change "NM" to -- Mn --

Column 30,
Line 23, after "0.2" please change "mmn" to -- mm --
Line 23, after "0.4 mm" please insert -- . --

Column 33,
Line 44, after "about 33 mm" please insert -- . --

Column 34,
Line 51, before "stainless steel" please change "M-355" to -- AM-355 --

Signed and Sealed this

Thirteenth Day of January, 2004

JON W. DUDAS
*Acting Director of the United States Patent and Trademark Office*